(12) United States Patent
Swetlin et al.

(10) Patent No.: US 7,557,167 B2
(45) Date of Patent: *Jul. 7, 2009

(54) POLYESTER COMPOSITIONS, METHODS OF MANUFACTURING SAID COMPOSITIONS, AND ARTICLES MADE THEREFROM

(75) Inventors: Brian J. Swetlin, Coatesville, PA (US); Kenneth A. Mazich, Newark, DE (US); Shaun Adkins Leone, Elkton, MD (US)

(73) Assignee: Gore Enterprise Holdings, Inc., Newark, DE (US)

( * ) Notice: Subject to any disclaimer, the term of this patent is extended or adjusted under 35 U.S.C. 154(b) by 464 days.

This patent is subject to a terminal disclaimer.

(21) Appl. No.: 11/541,514

(22) Filed: Sep. 28, 2006

(65) Prior Publication Data

US 2008/0081881 A1    Apr. 3, 2008

(51) Int. Cl.
C08G 63/00     (2006.01)
C08J 9/00      (2006.01)

(52) U.S. Cl. .................. 525/424; 525/172; 521/50; 528/271; 528/272

(58) Field of Classification Search .......... 525/424, 525/172; 528/271, 272; 521/50
See application file for complete search history.

(56) References Cited

U.S. PATENT DOCUMENTS

| | | | |
|---|---|---|---|
| 1,779,367 A | 10/1930 | Bruson | |
| 2,012,267 A | 8/1935 | Carothers | |
| 4,734,467 A * | 3/1988 | Yamada et al. | 525/440.02 |
| 5,098,776 A | 3/1992 | Kobayashi et al. | 428/283 |
| 5,889,140 A | 3/1999 | Watanabe | 528/354 |
| 6,045,694 A | 4/2000 | Wang et al. | 210/500.37 |
| 6,160,084 A | 12/2000 | Langer et al. | 527/272 |
| 2003/0032764 A1 * | 2/2003 | Cook et al. | 528/295.5 |

(Continued)

FOREIGN PATENT DOCUMENTS

CN     1640909 A     12/2004

(Continued)

OTHER PUBLICATIONS

ISO Standard No. 10993-6:1994(E) Biological evaluation of medical devices, Part 6: Tests for local effects after implantation, pp. 1-11.

(Continued)

*Primary Examiner*—Randy Gulakowski
*Assistant Examiner*—Alicia M Toscano
(74) *Attorney, Agent, or Firm*—Richard W. Ellis

(57) ABSTRACT

Crosslinked polymer compositions have backbones with first and second divalent saturated aliphatic moieties, a divalent saturated aliphatic secondary alcohol moiety, and a trivalent saturated aliphatic moiety. Hydrolytically labile ester bonds joined together these moieties. These polyesters may be polycondensation reaction products of a diol, a triol and a diacid. A molar ratio of the first divalent saturated aliphatic moiety, the divalent saturated aliphatic secondary alcohol moiety, and the trivalent saturated aliphatic moiety to the second divalent saturated aliphatic moiety is in the range of about 0.85 to about 1.5. Preferably, these polyesters are non-cytotoxic, biocompatible, bioabsorbable, or exhibit shape memory behavior with at least one transition temperature of greater than about 30° C. and less than about 100° C. and most preferably exhibit each of these qualities. The compositions may be adapted for a wide variety of uses, including medical applications.

40 Claims, 12 Drawing Sheets

U.S. PATENT DOCUMENTS

| | | | |
|---|---|---|---|
| 2003/0118692 A1 | 6/2003 | Wang et al. | 426/6 |
| 2004/0082733 A1* | 4/2004 | Algrim et al. | 525/437 |
| 2006/0036045 A1 | 2/2006 | Wilson et al. | 525/452 |

FOREIGN PATENT DOCUMENTS

| | | |
|---|---|---|
| WO | WO03/089492 | 10/2003 |

OTHER PUBLICATIONS

K. Ueberreiter and K Janders, Crystallization Kinetics of Polymers, Communication V: Properties and Crystallization Behavior of a Branched to Cross Linked Polyethylene Succinate, Kolloid-Zeitschrift & Zeitschrift fur Polymere 222(2): pp. 97-102, Feb. 1968.

Wenshou Wang, Peng Ping, Xuesi Chen, Xiabin Jing, Polyactive-base polyurethane and its shape-memory behaviour, Science Direct, European Polymer Journal 42 (2006) 1240-1249.

Xiaotong Zheng, Shaobing Zhou, Xiaohong Li, Jie Weng, Shape memory properties of poly(D, L-lactide)/hydroxyapatite composites, Science Direct, Biomaterials 27 (2006) 4288-4295.

Database WPI Week 199519, Derwent Publications Ltd., London, GB; AN 1995-144917 XP002475628 & JP 07 070296 A (Showa High Polymer Co Ltd) Mar. 14, 1995 abstract.

* cited by examiner

POLYESTER COMPOSITIONS, METHODS OF MANUFACTURING SAID COMPOSITIONS, AND ARTICLES MADE THEREFROM

FIELD OF THE INVENTION(S)

The present application relates to polymer compositions, specifically to polyesters, and more specifically to crosslinked polyesters that are the products of polycondensation reactions of a diol, a triol and a diacid, methods of manufacturing said compositions, and articles made therefrom.

BACKGROUND OF THE INVENTION(S)

Biocompatible and bioabsorbable in vivo synthetic polymers are known for use in the manufacture of implantable medical devices. Many such bioabsorbable polymers belong to the polyester family. For example, aliphatic polyesters have been used in drug delivery systems.

Known biodegradable polyester polymer/copolymer materials include polydioxanone (PDS), polyglycolic acid (PGA), poly-L-lactic acid (PLA), and copolymers of polyglycolic acid and either L-lactic acid or trimethylene carbonate (TMC).

Linear polyesters may be synthesized by ring opening polymerization of cyclic esters or lactones, or by polycondensation of one or more difunctional monomers. Polycondensation of difunctional monomers include the esterification of diacid chlorides and diols, or the ester exchange reaction of diesters and diols. Crosslinked polyesters can be formed by including in the polycondensation reaction monomers with functionalities greater than two.

U.S. Pat. No. 1,779,367 discloses condensation reaction products of certain higher polybasic acids and polyhydric alcohols, notably glycerol. In one example, 1 mole equivalent gylcerol and 1.5 mole equivalents sebacic acid are reacted.

U.S. Pat. No. 2,012,267 discloses alkylene ester reaction products of polybasic acids. These esters are said to be formed by the esterification of dibasic acids and glycols of the formula:

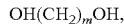

where "m" is an integer greater than 2. In example 5, poly (ethylene sebacate) is prepared from 67.3 g of sebacic acid and 21.7 g of ethylene glycol.

U.S. Pat. No. 5,098,776 discloses fibrous sheets having shape memory properties. The sheet comprises a natural or synthetic fiber and a layer formed by applying a powder of shape memory polymer. The shape memory polymer may be a urethane polymer, a styrene butadiene polymer, a crystalline diene polymer, and a norbornane polymer. To impart shape memory properties, a powder of shape memory polymer is applied to a part of the sheet with the aid of adhesive.

U.S. Pat. No. 5,889,140 discloses molded articles made from crosslinkable polylactone-based compositions having biodegradability and shape memorizable properties. The compositions are made from 100 parts by weight of polylactone (A) having a number average molecular weight of 10,000 to 300,000 and 0.1 to 30 parts by weight of crosslinkable monomer (B). The crosslinkable polylactone-based composition is crosslinked by irradiating active energy radiation or by heating at 120° C. to 250° C.

U.S. Pat. No. 6,160,084 discloses biodegradable shape memory polymers. In one embodiment, the compositions contain hard and soft segments. The hard segments have a higher transition temperature than the soft segments. The hard segments have a transition temperature of between −30° C. and 270° C. Either the hard or soft segments are crosslinkable.

U.S. Pat. Publ. No. 2003/0118692 discloses biodegradable polymer condensation products of glycerol and diacid (e.g., sebacic acid). The degradation rate is reputed by this publication to be adjustable by modifying crosslink density. The molar ratio of glycerol to the diacid disclosed may be between (1 and 1.5):1. This publication reports the manufacture of a poly(glycerol-sebacate) by polycondensation of equi-molar amount of glycerol and sebacic acid. The publication also reports that the resulting polymer has two crystallization temperatures at −52.14° C. and −18.50° C., has two melting temperatures at 5.23° C. and 37.62° C., and is totally amorphous at 37° C. The disclosed polymer is suggested for use as a tissue engineering construct, or in other medical and non-medical applications. This publication does not report any shape memory properties for this material.

Chinese Pat. Publ. No. 1 640 909 A discloses biodegradable ternary aliphatic polyester elastomers. An esterification reaction is carried out between a dibasic acid and a diol to form a low-molecular weight linear prepolymer. In this reaction, the molar ratio of the dibasic acid to diol is between (1.5 and 3.5):1. An esterification crosslinking reaction then is carried out between that linear prepolymer and a monomeric polyol. This patent publication does not report any shape memory properties for this material, and instead describes the resulting polyester as an elastomer.

SUMMARY OF THE INVENTION(S)

Crosslinked polymer compositions, specifically crosslinked polyesters, methods of manufacturing said compositions, and articles made therefrom are described.

In one aspect, the present application provides a crosslinked polycondensation product of a polyol and at least one saturated linear aliphatic diacid or derivative thereof. The polyol includes saturated aliphatic triol and saturated aliphatic diol. Preferably, the polyol includes glycerol and one of: ethylene glycol, 1,3 propanediol and 1,4 butanediol. Preferably, the aliphatic diacid or derivative thereof is sebacic acid. A molar ratio of moles saturated aliphatic triol to moles total polyol is in the range of about 0.2 to about 0.8. A molar ratio of moles total polyol to moles diacid is in the range of about 0.85 to about 1.5.

In another aspect, the present application provides a polymer composition with a backbone having a first and a second divalent saturated aliphatic moiety, a divalent saturated aliphatic secondary alcohol moiety, a trivalent saturated aliphatic moiety, and ester linkages between the moieties. A molar ratio of the sum of (1) a number of moles of the first divalent saturated aliphatic moiety, (2) a number of moles of the divalent saturated aliphatic secondary alcohol moiety, and (3) a number of moles of the trivalent saturated aliphatic moiety to a number of moles of the second divalent saturated aliphatic moiety is in the range of about 0.85 to about 1.5. In another aspect, the present application provides a method of manufacturing a crosslinked polyester composition via a polycondensation reaction of (a) polyol, comprising saturated aliphatic triol, and saturated aliphatic diol, and (b) a linear aliphatic diacid or derivative thereof (e.g., a diester of saturated linear aliphatic diacid, or a diacyl halide of a saturated linear aliphatic diacid), or mixtures thereof. Component (a), the polyol, may comprise glycerol and ethylene glycol, and preferably is present in a molar ratio of moles triol to moles total polyol of between about 0.20 and 0.80. Component (b), the diacid or diacid derivative, may comprise sebacic acid, and preferably is present in a molar ratio of polyol to diacid of between about 0.85 to about 1.5.

In yet another aspect, the present application provides an article having a crosslinked polyester composition, which preferably exhibits shape memory properties, and more preferably has at least one transition temperature of greater than about 30° C. and less than about 100° C.

In still another aspect, the present application provides a porous article or foam, e.g., foamed or sponge-like porous material having cell walls comprising a crosslinked polyester composition. Preferably, the foamed or sponge-like porous material exhibits shape memory properties, and more preferably has at least one transition temperature of greater than about 30° C. and less than about 100° C.

In yet still another aspect, the present application provides a composite having a macroscopic combination of a crosslinked polyester composition with at least one other material. Preferably, the other material is a film material, a fibrous material, a porous membrane material, or combinations thereof. Preferably, the crosslinked polyester composition, the composite or both exhibit shape memory properties, and more preferably, the crosslinked polyester composition has at least one transition temperature of greater than about 30° C. and less than about 100° C. In another aspect, the present application provides a composite having a macroscopic combination of polytetrafluoroethylene (PTFE) and a shape memory polymer. Preferably, the PTFE is expanded PTFE (ePTFE). Preferably, the shape memory polymer exhibits shape memory behavior upon heating to at least one transition temperature of greater than about 30° C. and less than about 100° C. More preferably, the shape memory polymer is a crosslinked polyester composition.

DETAILED DESCRIPTION OF THE PREFERRED EMBODIMENTS

Figure 1:
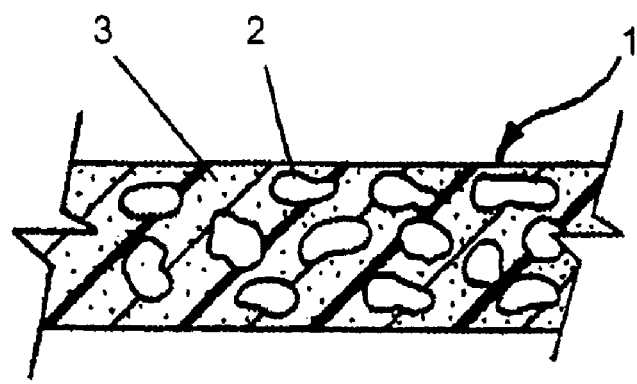
FIG. 1 is a schematic representation of an exemplary closed cell porous foam product.

Certain exemplary embodiments of the present invention(s) will be described below and detailed in the examples and with reference to the accompanying drawings. The present invention(s) may, however, be embodied in many different forms and should not be construed as limited to the embodiments set forth herein.

As used throughout the specification, the following terms shall have the following meanings, unless the context clearly indicates otherwise. By "Bioabsorbable" is meant a material that is capable of being degraded over time when placed in a living body (e.g., through enzymatic, hydrolytic or other chemical reactions) into products which are metabolized, assimilated or excreted from the body.

By "Biocompatible" is meant a material that invokes no adverse tissue reactions at the implant site in a majority of mammals after implantation. Biocompatibility may be evaluated with reference to International Standards Organization (ISO) Standard No. 10993 Part 6: Tests for local effects after implantation, First Ed., July, 1994.

By "medical device" is meant an instrument, apparatus, contrivance, implant, implement, machine, or other similar or related article, including, but not limited to, any accessory, component, kit or part, which is used in the cure, diagnosis, mitigation, prevention, or treatment of disease, in man or other animals, or intended to affect the structure or any function of the body of man or other animals. Such medical devices include, but are not limited to, aneurysm repair devices, cannulae, catheters, endoprostheses, hernia plugs, implants, occlusive devices, periodontal repair materials, pledget materials, prostheses, septal occlusive devices, shunts, stents, surgical repair patches, sutures, tubes, vascular grafts, vascular occlusion devices, vascular patches, wound dressings and the like.

By "shape memory behavior" is meant that a material capable of storing or memorizing a first shape so that the polymer may be deformed to and maintains a second shape until appropriately stimulated (e.g., by heating above a transition temperature), after which the polymer tends to revert from the second shape to the first shape. It also may be possible to stimulate shape memory behavior with other stimuli, e.g., by changes in pH, electrical stimuli, light stimuli.

By "transition temperature" is meant a temperature range where a material is subject to a phase transition, which, in the case of polymeric materials, means the polymeric materials are completely amorphous above the transition temperature and may be crystalline or semi-crystalline below the transition temperature. The phase change can be determined by a conventional Differential Scanning Calorimetry (DSC) scan of the material.

Backbones of the crosslinked polymer compositions described below are comprised of four monomeric repeating units. A first monomeric repeating unit is a divalent aliphatic moiety. A second monomeric repeating unit is a divalent aliphatic alcohol moiety. A third monomeric repeating unit is a trivalent aliphatic moiety. A fourth monomeric repeating unit is another divalent aliphatic moiety, which may be the same or different from the first monomeric repeating unit.

These monomeric repeating units are joined together by hydrolytically labile ester bonds. Alternatively, other hydrolytically labile bonds, under physiological conditions, may join the monomer repeating units including, but not limited to, amide, carbonate, thioamide, thioester, and urethane linkages, among others.

The amounts of the monomeric repeating units and the ester linkages may be varied to achieve crosslinked polyester compositions having properties appropriate for various applications. Preferably, the first, second and third monomeric repeating units are, independently, present in the final polymer composition in an amount of about 4 to about 30 mol %. Preferably, the fourth monomeric repeating unit is present in the final polymer composition in an amount about 20 to about 30 mol %. Preferably, the ester linkages are present in the final polymer composition in an amount of about 35 to about 55 mol %.

The first monomeric repeating unit ($R_1$) has the formula:

where a is an integer between 2 and 35, preferably between 2 and 20 and more preferably between 2 and 10.

The second monomeric repeating unit ($R_2$) has the formula:

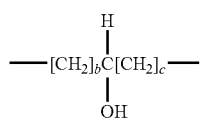

where b and c are, independently, integers between 1 and 35, preferably between 1 and 20 and more preferably between 1 and 10.

The third monomeric repeating unit ($R_3$) has the formula:

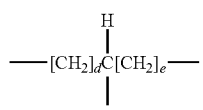

where d and e are, independently, integers between 1 and 35, preferably between 1 and 20 and more preferably between 1 and 10.

The fourth monomeric repeating unit ($R_4$) has the formula:

where f is an integer between 2 and 35, preferably between 2 and 20 and more preferably between 2 and 10.

Most preferably, the value of integer a is 2, the values of integers b, c, d and e are identical and are 1, and the value of integer f is 8.

A molar ratio, $\varphi$, is given by the formula:

$$\varphi = \frac{[\text{moles } R_2 + \text{moles } R_3]}{[\text{moles } R_1 + \text{moles } R_2 + \text{moles } R_3]}$$

$\varphi$ is preferably in the range of 0.20 to 0.80. When the crosslinked polymer compositions are random polymers, $\varphi$ is more preferably $0.20 \leq \varphi \leq 0.65$, and most preferably $0.20 \leq \varphi \leq 0.50$. When the crosslinked polymer compositions are non-random polymers, $\varphi$ is more preferably $0.50 \leq \varphi \leq 0.80$.

A molar ratio, $\beta$, is given by the formula:

$$\beta = \frac{[\text{moles } R_1 + \text{moles } R_2 + \text{moles } R_3]}{[\text{moles } R_4]}$$

$\beta$ is preferably in the range of 0.85 to 1.5, more preferably $0.87 \leq \beta \leq 1.35$, and most preferably $0.9 \leq \beta \leq 1.2$.

A density, $\rho$, of the crosslinked polymer compositions (exclusive of additives) is in the range of 0.05 grams per cubic centimeter (g/cc) to 1.50 g/cc (exclusive of any additives). The crosslinked polymer compositions may be made into a foamed or sponge-like porous material by, for example combining the crosslinked polymer compositions with a gas, such as air. The foamed or sponge-like materials have a density less than about 0.80 g/cc, preferably have a density in the range of about 0.1 g/cc to about 0.3 g/cc.

Preferably, the crosslinked polymer compositions have residual acidity in concentrations of greater than about 0.0001 milliequivalents of acid per gram of composition (meq. acid/gram) and less than about 1.0 meq. acid/gram or less, more preferably in concentrations less than about 0.5 meq. acid/gram, and most preferably in concentrations less than about 0.3 meq. acid/gram measured by titration.

Residual acid, when present in the crosslinked polymer compositions, provides ion exchange properties, and thus the crosslinked polymer compositions may form ionic salts with cationic, polycationic and zwitterionic species. These cationic, polycationic and zwitterionic species include, but are not limited to, aluminum ions, amino acids, amino sugars, ammonium ions, barium ions, calcium ions, chitin, chitosan, copper ions, ferric ions, ferrous ions, magnesium ions, peptides, polyethyleneimine, polypeptides, potassium ions, primary amino compounds, quaternary amine compounds, quaternary ammonium compounds, secondary amino compounds, sodium ions and combinations thereof.

Residual acid groups and residual hydroxyl groups also may be reacted with organic compounds, bio-organic compounds and pharmaceutical compounds to modify the biological properties of the compositions. Conjugation reactions may modify the biological properties of the crosslinked polymer compositions. Such biological properties include, but are not limited to, angiogenesis properties, anti-scarring properties, bactericidal properties, blood coagulation properties, cellular adhesion properties, cellular growth properties, cellular migration properties, cellular morbidity properties, cellular targeting properties, infection prevention properties, thrombogenic properties, tissue generation properties, tissue in-growth properties, and wound healing properties.

Residual acid groups and residual hydroxyl groups may be quantified by various well known analytical procedures. For example, residual unreacted hydroxyl groups will be apparent in the infrared spectra of the crosslinked polymer compositions. Titration methods also may be used to quantify said residual unreacted hydroxyl and carboxylic acid groups. For example, residual unreacted carboxylic acid groups of the crosslinked polymer compositions may be quantified by titration with a strong base, such as potassium hydroxide.

The Young's modulus at 22° C. preferably is greater than 2.5 Megapascals (MPa). Where the crosslinked polymer composition is a random polymer, the Young's modulus is more preferably greater than about 6.0 MPa, and most preferably greater than about 40 MPa. Where the crosslinked polymer composition is non-random, the Young's modulus is more preferably greater than about 5.0 MPa and most preferably greater than about 6.0 MPa. The Young's modulus is lower at 37° C. than at 22° C. The elastic modulus at 37° C. preferably is in the range of about 0.1 to about 200 MPa, more preferably is in the range of about 1 to about 25 MPa, and most preferably is in the range of about 2.5 to about 10 MPa.

The crosslinked polymer compositions degrade via hydrolysis. Hydrolysis may be catalyzed or not. Hydrolysis catalysts may include, but are not limited to, enzymes (particularly lipases and esterases). Hydrolysis may be demonstrated in water, saline, blood serum or aqueous solutions of enzymes. Hydrolysis may be affected by biological life forms such as bacteria, fungi, and molds. Hydrolysis is also affected in-vivo, such as when the crosslinked polymer compositions are implanted in a mammal. Hydrolysis is accompanied by weight loss. Hydrolysis leads to the production of various reaction products including diols, triols and diacids from which the crosslinked polymer compositions may have been produced. These reaction products may be further degraded, metabolized, assimilated or excreted in-vivo. Preferably, the crosslinked polymer compositions are biocompatible, bioabsorbable and/or non-cytotoxic.

The chain microstructural sequence, or "order," of the units may be random or non-random. These microstructural sequences can affect properties of the crosslinked polymer compositions. Non-random microstructural sequences may be described as block or multi-block chain microstructures. The chain order may be characterized by various analytical methods, such as nuclear magnetic resonance (NMR) spectroscopy.

The crosslinked polymer compositions may be homogeneous or phase separated (i.e., characterized by a macroscopic topology or structural morphology where chains rich in a particular monomeric repeating unit are spatially segregated from chains rich in another monomeric repeating unit). Various analytical methods may be used to characterize whether the crosslinked polymer compositions are homogenous or phase separated. These methods include, but are not limited to, calorimetry, dilatometry, light scattering spectroscopy, microscopy, and thermal mechanical analysis. The crosslinked polymer compositions may be amorphous or semicrystalline at temperatures greater than about 20° C. to less than about 25° C. Preferably, the crosslinked polymer composition exhibits crystallization upon cooling from a temperature of about 100° C. to a temperature of about 20° C. at a rate of 2° C./min.

Preferably, the crosslinked polymer compositions are semicrystalline at temperatures in the range of greater than about 20° C. to less than about 25° C. In these preferred embodiments, the volume fraction or weight fraction of the crystalline phases may be in the range 0.05 to 0.95. Various well known analytical methods (e.g., calorimetry, dilatometry, X-ray diffraction and microscopy) may be used to characterize whether compositions are crystalline/semicrystalline.

Those crosslinked polymer compositions that are semicrystalline at temperatures in the range of greater than about 20° C. to less than 25° C., are preferably totally amorphous at temperatures greater than near physiological temperatures, e.g., above temperatures greater than about 30° C. When the crosslinked polymer compositions are totally amorphous at near physiological temperatures, this enables, among other things, shape memory behavior stimulation by body heat.

More preferably, such crosslinked polymer compositions are totally amorphous above temperatures greater than about 35° C., and most preferably are totally amorphous above 35° C. and less than about 100° C. The higher temperature(s) may be advantageous for simplifying storage requirements and preventing unintentional activation of shape memory behavior. In this aspect, the shape memory behavior may be stimulated by external heat and other energy sources, as described more fully below. The semicrystalline to totally amorphous transition temperature of the crosslinked polymer compositions is a function of the reactants chosen, their relative proportion and the synthetic process path chosen.

Preferably, the crosslinked polyester compositions have at least one transition temperature of greater than about 30° C. and less than about 100° C., more preferably greater than about 30° C. and less than about 50° C., and most preferably greater than about 30° C. and less than about 45° C.

Preferably, the crosslinked polymer compositions exhibit shape memory behavior. These compositions maintain dimensional change in the absence of external forces in their semicrystalline state. If the material is semicrystalline when deformed, for example in cold drawn deformation, the shape is maintained without substantial change in crystallinity. If the material is amorphous when deformed, the deforming force is maintained while the shape memory material is caused to partially crystallize, by cooling for example.

Upon application of a stimulus, the shape change is at least partially recovered. The stimulus directly or indirectly induces a change in crystallinity. For example, the stimulus may include heat. The resulting temperature increase reduces crystallinity. In the crosslinked polymer compositions exhibiting shape memory behavior, this transformation may occur at any temperature greater than about 35° C. to less than about 100° C. The shape memory behavior may be manifested by a change in at least one dimension of the polymeric material in response to stimulus, or if the material is restrained, a change in the force necessary to maintain the shape of the material in at least one dimension upon application of stimulus, or both.

The crosslinked polymer compositions can be sterilized. Preferred sterilization methods include, but are not limited to, autoclave, ethylene oxide and gamma radiation. The most preferred sterilization method is gamma radiation. The preferred gamma radiation dosage is about 25 kiloGray (kGy) or less.

The crosslinked polymer compositions may contain various further ingredients, which may be added to the reactants before polymerization, during polymerization or after polymerization is completed. The quantity of such further ingredients optionally added to the crosslinked polymer compositions will preferably comprise less than about 25% of the composition by volume. More preferably, the quantity of said further ingredients comprises less than about 15% of the composition by volume. Most preferably, such further ingredients comprise less than about 5% of the composition by volume. The various further ingredients may be fillers or nano-materials (e.g., have at least one dimension which is 100 nanometers or less).

For example, ceramic, inorganic, metallic, organic, organometallic, pharmaceutical, and polymeric additives may be optionally added to the crosslinked polymer compositions as desired to modify the crosslinked polymer composition's acoustic properties, anti-scarring properties, bio-degradation properties, biological properties, color, crystallization kinetics, density, disease prevention properties, disease treatment properties, electrical properties, mechanical properties, optical properties, photo-degradation properties, processing behavior, surface properties, thermo-degradation properties, thermo-oxidative-degradation properties, wound healing properties, and combinations thereof.

Inorganic or metallic radio-opaque particles are one such additive, and may be dispersed into the crosslinked polymer compositions. Said radio-opaque particles include, but are not limited to, barium sulfate, gold, platinum, silver and combinations thereof. Preferably, said radio-opaque particles are present at a volume fraction less than about 0.30. More preferably, said radio-opaque particles are present at a volume fraction less than about 0.20. Most preferably, said radio-opaque particles are present at a volume fraction less than about 0.10.

Dyes or pigments are another additive that may be added to the crosslinked polymer compositions. By altering the color of the crosslinked polymer compositions, the compositions may be caused to absorb light energy (e.g., laser light) and thereby increase local temperature sufficient to selectively stimulate a transformation from the metastable state to the original or default shape, i.e., shape memory behavior. This may be advantageous where the crosslinked polymer compositions are desired to be deployed in small spaces, which may only be accessible via optical fibers (which can transmit light to the crosslinked polymer compositions). Alternatively, the crosslinked polymer compositions may be colored so that discrete regions have different light absorption characteristics than other regions. This permits different regions of the crosslinked polymer compositions to be activated utilizing light sources with discrete wavelengths that correspond to the particular absorption band.

Isocyanate or diisocyanate compounds are yet another additive. These compounds may be included in the crosslinked polymer composition to modify the density and to produce a foamed or sponge-like article. Nucleating agents are still another additive, which may be used to modify the crystallization kinetics of the crosslinked polymer compositions. A hydrophilic coating may be applied to the surface of articles prepared from the crosslinked polymer compositions to modify the surface properties. Combinations of various additives also may be used.

Where the labile bonds are ester bonds, the composition is a crosslinked aliphatic polyester. In that case, the structure of the backbone may consist essentially of linked ester units, A, B, and C. The linked ester units are of the formula:

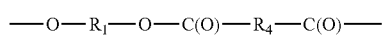

A

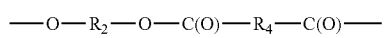

B

-continued

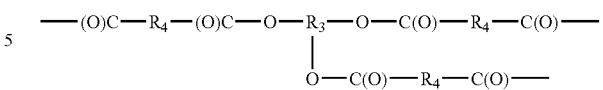

C where $R_1$, $R_2$, $R_3$ and $R_4$ are given by the formulas set forth above.

Such crosslinked aliphatic polyester may be the polycondensation reaction products of monomers containing hydroxyl groups and carboxylic acid groups. In these reactions, polymer chain growth proceeds by condensation reactions between molecules of all degrees of polymerization. For example, a diol with two hydroxyl groups, a diacid with two carboxylic acid groups, and a triol with three hydroxyl groups may be used. In that embodiment, ester unit A is a condensation product of an aliphatic diol and a linear aliphatic dicarboxylic acid, and ester units B and C are condensation products of aliphatic triols and linear aliphatic dicarboxylic acids.

It should be understood that alternatively, the polyester also may be the polycondensation reaction product of a diol with two hydroxyl groups, a diacid with two carboxylic acid groups and a triacid with three carboxylic acid groups.

In embodiments made from a diol, a diacid and a triol, $R_1$ is a linear sequence of covalently bonded methylene groups originating from an unsubstituted linear aliphatic diol. The linear sequence of methylene groups is covalently bonded at one end to an ester group. At the other end, the linear sequence of methylene groups may be covalently bonded either to an ester group or to a primary hydroxyl group. The ester group(s) is the reaction product of a primary hydroxyl group of an unsubstituted linear aliphatic diol and a carboxylic acid group of a linear aliphatic dicarboxylic acid. The primary hydroxyl group originates from an unsubstituted linear aliphatic diol.

In embodiments made from a diol, a diacid and a triol, $R_2$ is a linear sequence of covalently bonded carbon atoms originating from a linear aliphatic triol. The terminal carbon atoms of the linear sequence are each covalently bonded to two hydrogen atoms. The terminal carbon atom at one end of the linear sequence also is covalently bonded to an ester group, and the terminal carbon atom at the other end either is covalently bonded to an ester group or to a primary hydroxyl group. An intermediate carbon atom of the linear sequence of covalently bonded carbon atoms (e.g., the middle carbon atom when $R_2$ has three covalently bonded carbon atoms) is covalently bonded to a hydrogen atom and to a secondary hydroxyl group. The ester group(s) is the reaction product of a primary hydroxyl group of a linear aliphatic triol and a carboxylic acid group of a linear aliphatic dicarboxylic acid. The primary hydroxyl group originates from a linear aliphatic triol.

Also in embodiments made from a diol, a diacid and a triol, $R_3$ is a branched or crosslinked moiety. It is a linear sequence of covalently bonded carbon atoms originating from a linear aliphatic triol. The terminal carbon atoms of said linear sequence are each covalently bonded to two hydrogen atoms. Each of the terminal carbon atoms is covalently bonded to an ester group. These ester groups are the reaction products of a primary hydroxyl group of a linear aliphatic triol and a carboxylic acid group of a linear aliphatic dicarboxylic acid. An intermediate carbon atom of said linear sequence of carbon atoms (e.g., the middle carbon atom when $R_3$ has three covalently bonded carbon atoms) is covalently bonded to one hydrogen atom and to one ester group. The ester group is the reaction product of a secondary hydroxyl group of a linear aliphatic triol and a carboxylic acid group of a linear aliphatic dicarboxylic acid.

Also in embodiments made from a diol, a diacid and a triol, $R_4$ is a linear sequence of covalently bonded methylene groups originating from a linear aliphatic dicarboxylic acid. The linear sequence of covalently bonded methylene groups also is covalently bonded at one end of said sequence to a) an ester group that is the reaction product of a carboxylic acid group of a linear aliphatic dicarboxylic acid and a primary hydroxyl group of a unsubstituted linear aliphatic diol, or b) an ester group that is the reaction product of a carboxylic acid group of a linear aliphatic dicarboxylic acid and a primary hydroxyl group of a aliphatic triol, or c) an ester group that is the reaction product of a carboxylic acid group of a linear aliphatic dicarboxylic acid and a secondary hydroxyl group of a aliphatic triol. The linear sequence of covalently bonded methylene groups also is covalently bonded at the other end of said sequence to a) a carboxylic acid group originating from said linear aliphatic dicarboxylic acid, or b) an ester group that is the reaction product of a carboxylic acid group of a linear aliphatic dicarboxylic acid and a primary hydroxyl group of a preferred unsubstituted linear aliphatic diol, or c) an ester group that is the reaction product of a carboxylic acid group of a linear aliphatic dicarboxylic acid and a primary hydroxyl group of a aliphatic triol, or d) an ester group that is the reaction product of a carboxylic acid group of a linear aliphatic dicarboxylic acid and a secondary hydroxyl group of a aliphatic triol.

Linear aliphatic diols include, but are not limited to, unsubstituted linear aliphatic diols, such as 1,2-ethanediol (i.e., ethylene glycol), 1,3-propanediol, 1,4-butanediol, 1,5-pentanediol, 1,6-hexanediol, 1,7-heptanediol, 1,8-octanediol, 1,9-nonanediol, 1,10-decanediol and combinations thereof. Preferred unsubstituted linear aliphatic diols include 1,2-ethanediol, 1,3-propanediol, 1,4-butanediol, 1,2-ethanediol is most preferred.

Linear aliphatic triols include, but are not limited to, 1,2,3-trihydroxypropane, butane-1,2,4-triol and combinations thereof. Although other aliphatic triols may be used, a preferred aliphatic triol is 1,2,3-trihydroxypropane (i.e., glycerol).

Linear aliphatic dicarboxylic acids include, but are not limited to, 1,4-butanedioic acid, 1,5-pentanedioic acid, 1,6-hexanedioic acid, 1,7-heptanedioic acid, 1,8-octanedioic acid, 1,9-nonanedioic acid, 1,10-decanedioic acid, 1,11-unedecanedioic acid, 1,12-dodecanedioic acid and combinations thereof. More preferred linear aliphatic dicarboxylic acids are 1,4-butanedioic acid (i.e., succinic acid), 1,6-hexanedioic acid (i.e., adipic acid) and 1,10-decanedioic acid (i.e., sebacic acid). A most preferred linear aliphatic dicarboxylic acid is sebacic acid. Preferably, the aliphatic dicarboxylic acids are unsubstituted.

The dicarboxylic acids may be used in the form of one or more of their corresponding diester derivatives, particularly their dimethanol or diethanol ester derivatives. The dicarboxylic acids also may be used as one or more of their corresponding diacyl halide derivatives, particularly their diacyl chloride derivatives. The dicarboxylic acid may be used as a corresponding anhydride. For example, succinic anhydride may be used instead of 1,4-butanedioic acid.

In addition to the aforementioned preferred unsubstituted linear aliphatic diols, linear aliphatic triols and linear aliphatic dicarboxylic acids, the crosslinked polymer compositions may include linear aliphatic α,ω-hydroxyacids or their corresponding cyclic dimers, such as glycolic acid, glycolide, lactic acid, lactide, β-hydroxypropanoic acid, γ-hydroxybutanoic acid and combinations thereof. Preferably, said linear aliphatic α,ω-hydroxyacids or their corresponding cyclic dimers are present at a molar fraction less than about 0.25, more preferably less than about 0.15, and most preferably less than about 0.05.

Multiple ester linked units A, B and C are covalently connected via ester groups to produce the crosslinked aliphatic polyester compositions. Ester linked units A, B and C may be arranged via a multiplicity of covalent ester connections in any possible chain microstructural sequence. An ester linked unit A may be covalently connected to: a) another ester linked unit A, b) an ester linked unit B, or c) an ester linked unit C. Likewise, an ester linked unit B may be covalently connected to a) an ester linked unit A, or b) another ester linked unit B, or c) an ester linked unit C. An ester linked unit C may be covalently connected to a) an ester linked unit A, or b) an ester linked unit B.

Phase separated crosslinked polyester compositions may have a macroscopic topology or structural morphology with submicron to micron sized spatially distinct regions. For example, there may be chains rich in ester linked unit A dispersed within, or co-continuous with, regions having chains rich in ester linked unit B. Alternatively, this macroscopic topology or structural morphology also may be manifested by submicron to micron sized spatially distinct regions having chains rich in ester linked unit B dispersed within, or co-continuous with, regions having chains rich in ester linked unit A.

Unreacted primary and secondary hydroxyl groups and carboxylic acid groups may be present within the crosslinked polyester compositions. These unreacted groups provide a means by which the crosslinked polyester compositions may be chemically modified. Chemical modification may be affected by reaction with any compound capable of reacting with primary hydroxyl, secondary hydroxyl or carboxylic acid groups.

The compositions described above may be produced under typical conditions for polycondensation reactions of polyols and diacids. The polycondensation reaction may be catalyzed or not. If catalyst(s) is used, preferably it is biocompatible, and more preferably it is bioabsorbable. The particular process conditions chosen will depend on numerous factors including, but not limited to, the desired properties of the final product, the viscosity of the reaction mixture and the melting temperature of the polymer or monomer reactants.

Degree of conversion is a measure of the extent of monomeric reaction in the reaction mixture. The degree of conversion can be quantified by various techniques known in the art. For example, the reaction may be monitored by measuring the amount of byproduct water evolved. Alternatively, titration of residual carboxylic acid may be used to monitor the reaction.

To increase degree of conversion, the reactions may be conducted at elevated temperatures and/or under inert gas blanket (e.g., nitrogen gas). Continuous removal of byproduct(s) also may increase degree of conversion; vacuum or nitrogen blanket are useful in this regard. The reactions generally are conducted above 120° C. Increasing the reaction temperature will reduce the reaction times required to attain a particular degree of conversion.

The crosslinked polyester compositions may be produced by different polycondensation processes. Monomeric triol, diol and diacid may be combined at elevated temperature(s) such that the monomer mixture is reacted. In a one stage process, the reaction is driven directly to the desired degree of conversion beyond a gel point. This may be preferable if the material is to be used for molding, combination or in circumstances where other isolation unit operation is not desired.

In a two stage process, the first step is the above-described initial reaction, which is stopped at a degree of conversion below the gel point to yield an intermediate reaction product. The intermediate reaction product may be a waxy solid at room temperature and may be used to mold polymer solids, or may be combined with porogen to produce polymer foams, or may be macroscopically combined with other materials to produce composite structures, or may be combined with diisocyanates to produce urethane linked foams as described below. In the second stage of this method, the polymerization reaction is driven beyond the gel point to yield a crosslinked polymeric product.

Preferably, the second stage polymerization reaction is continued until the unreacted carboxylic acid is present at a concentration less than about 1.0 meq. acid/gram, more preferably less than 0.5 meq. acid/gram to yield the crosslinked polymer compositions, and most preferably less than 0.3 meq. acid/gram.

Alternatively, the crosslinked polymer compositions may be produced so that the chain microstructural sequence or "order" of the units is non-random. In this process, uncrosslinked polymer intermediates are first made. Then, these intermediates are melt mixed in appropriate proportions and subsequently driven beyond the gel point to yield crosslinked polymeric compositions.

For example, in this process a first polymer may be made from a diacid and a diol, and a second polymer made from a diacid and a triol. Most generally, these initial polymer reactions are stopped before the degree of conversion is beyond the gel point. Then the two polymers are mixed together under conditions favorable to further polymerization such that the intermediate polymers become crosslinked to one another. It should be appreciated that these intermediate polymers may or may not be homopolymers.

Porous articles or foams may be formed of the crosslinked polymer compositions such as depicted in FIG. 1. This porous foam (1) has a structure that includes voids or pores (2). These may be called cells. In FIG. 1, the cells are depicted as closed cells, cell walls, or surfaces of the bubbles, are not broken. It should be understood that the foamed or sponge-like porous materials may be of closed cell, open cell or hybrid cell type. The walls of these cells comprise crosslinked polymer compositions (3). Porous articles of the crosslinked polymer compositions may exhibit shape memory behavior or not.

Porous articles may be prepared by methods and techniques known in the art, such as solvent casting, entraining air, porogen removal, $CO_2$ foaming and like processes.

An illustrative porogen removal process for producing porous articles also will now be described. A porogen may be a solid, liquid, or gaseous material that is removable from the polymer composition to create pores or voids, thereby lowering the effective density of the resulting material. Exemplary porogens include, but are not limited to, collagen, gelatin, inorganic salt (e.g., potassium chloride, sodium chloride, sodium citrate, sodium tartrate), paraffin, saccharose and combinations thereof. The size and shape of the porogen particles will affect the size and shape of the resulting pores, and the polymer to porogen ratio is correlated to the amount of porosity of the final structure.

Preferably, when porous articles are prepared by porogen removal, the porogen is selected so that it can be removed by using a non-cytotoxic solvent (e.g., water). Alternatively, the porogen may be selected so that the solvent, although potentially cytotoxic, does not remain in the porous article after appropriate processing.

For example, sodium chloride may be used as a porogen to create pores that correspond to the individual salt crystals. In a salt-bed process, an intermediate reaction product is distributed through a bed of salt crystals. The intermediate product may be further polymerized. The salt crystals may be removed by rinsing, for example, with deionized water. The salt crystals or other porogen may be removed by an appropriate process before the polymer is fully crosslinked, or after crosslinking.

The porous articles may include urethane linked foams. Urethane linked foams may be prepared from the uncrosslinked intermediate reaction products described above. For example, diisocyanate may be added to molten intermediate. Such diisocyanates react to form urethane and urea linkages. Exemplary urethane and urea linkages are:

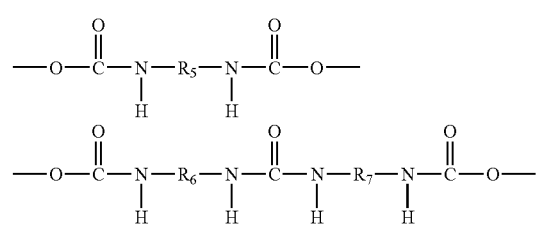

where $R_5$, $R_6$, and $R_7$, are each independently a divalent aromatic or aliphatic moiety. An exemplary diisocyanate is 4,4'-methylenebis(phenyl isocyanate).

The final foam density is a function of the weight fraction of diisocyanate added to the intermediate. Preferably, the urethane and urea linkages comprise about 15 mole % of less of the polymer composition.

These foams may be semicrystalline or amorphous at room temperature. Such foams may exhibit shape memory behavior or not, and may be nontoxic to mammalian cells.

The crosslinked polymer compositions are advantageously macroscopically combined with other materials to construct composites, such as fibrous composites, laminates, and particulate composites. The other materials may be continuously or discontinuously distributed within the crosslinked polymer compositions. Alternatively, the crosslinked polymer compositions may be continuously or discontinuously distributed within the other materials.

Numerous fabrication methods and techniques are known in the art for manufacturing composites. For example, the crosslinked polymer compositions can be coated on, laminated to, or imbibed within these other materials to form a composite. Preferably, the crosslinked polymer compositions contact the other materials. These other materials can have various forms and shapes. Illustrative forms include fibers, particles, rods, sheets and tubes.

These composites may incorporate various other materials, such as film materials, fibrous materials and porous membrane materials. Preferably, these other materials are a fluoropolymer, more preferably, polytetrafluoro-ethylene, and most preferably expanded polytetrafluoroethylene. Alternatively, these other materials preferably are bioabsorbable, more preferably are poly(glycolide-co-trimethylene-carbonate) (PGA/TMC).

The composites and/or the other materials may exhibit shape memory behavior or not. The composites and/or the other materials may be biocompatible or not. The composites and/or the other materials may be degradable via hydrolysis or not. Preferably, the composites and other materials are biocompatible and/or bioabsorbable. Preferably, the crosslinked polymer compositions impart shape memory properties to the final composites.

Figure 2:
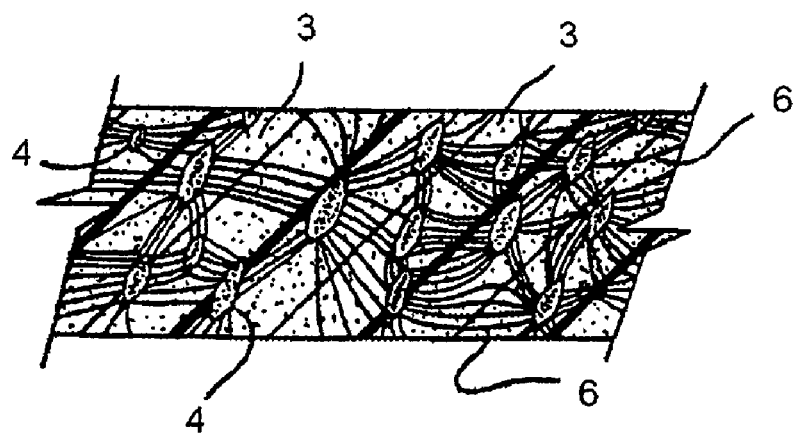
FIG. 2 is a schematic representation of an exemplary composite construction with imbibed ePTFE.

Referring to FIG. 2-6, various composites are constructed in accordance with the present application as shown. FIG. 2 shows an imbibed ePTFE composite. The ePTFE material has a microstructure of interconnected fibrils that defines micropores. The microstructure includes nodes (4) and fibrils (6). A crosslinked polymer composition (3), such as described herein, has been imbibed into the microstructure. Preferably, the crosslinked polymer composition (3) is securely adhered to both the external and internal surfaces, i.e., the fibrils and/or nodes of the ePTFE material. The imbibing may be partial or full. When full or complete imbibing has been accomplished, the structure of the imbibed ePTFE composite may consist essentially of PTFE and crosslinked polymer compositions described herein.

Figure 3:
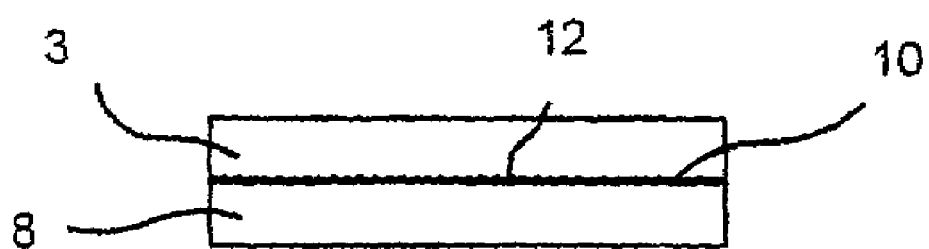
FIG. 3 is a schematic representation of an exemplary composite construction having ePTFE coated with crosslinked polymer composition on one side.
Figure 4:
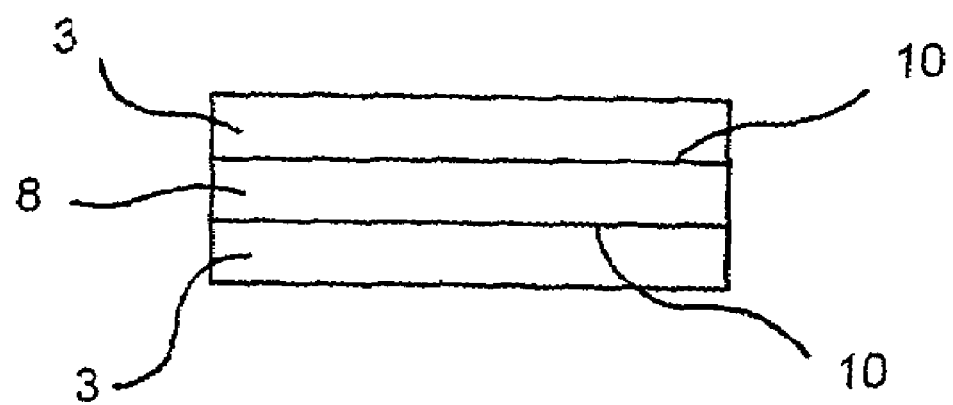
FIG. 4 is a schematic representation of an exemplary composite construction having ePTFE coated with crosslinked polymer composition on two sides.
Figure 5:
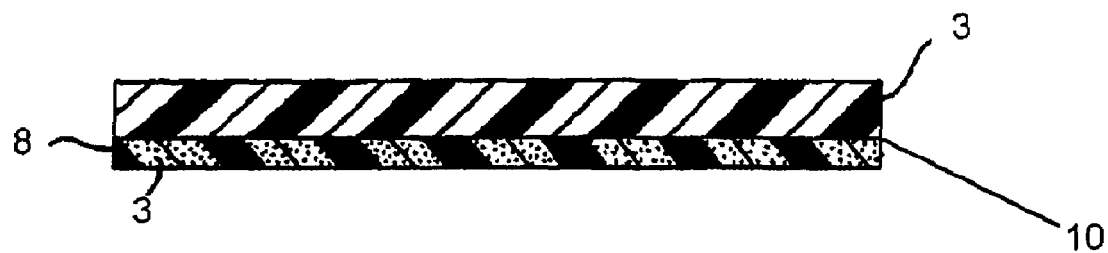
FIG. 5 is a schematic representation of an exemplary composite construction having ePTFE coated with crosslinked polymer composition on one side and imbibed into the ePTFE.
Figure 6:
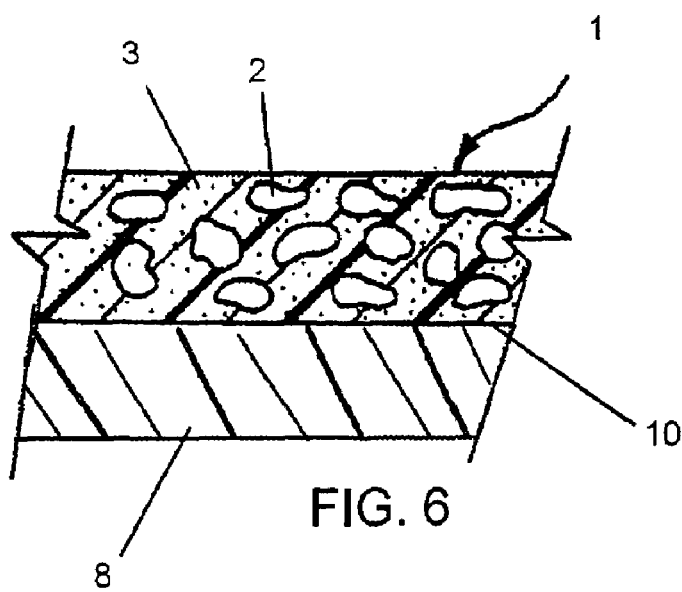
FIG. 6 is a schematic representation of an exemplary porous, laminated foam product.

In FIG. 3, an ePTFE material portion (8) is joined with a crosslinked polymer composition portion (3). In FIG. 4, an ePTFE material portion (8) is between two crosslinked polymer composition portions (3). Between the ePTFE material portion (8) and the crosslinked polymer composition portion (3) is defined an interface (10). It also is possible to imbibe ePTFE (8) with a polymer composition (3) that is subsequently crosslinked, and also to join that imbibed ePTFE to a second crosslinked polymer composition portion (3) as shown in FIG. 5. The two crosslinked polymer compositions may be the same or different. In FIG. 6, porous foam (1) with cells (2) is made of a crosslinked polymer composition (3) as described herein and is joined to another material (8).

For some applications, it may be desirable to provide an adhesive or compatibilizing compound (12) at the interface as shown in FIG. 3.

Fibrous composites may be formed by combining the crosslinked polymer compositions with fibrous materials. The fibrous materials may be discontinuous (randomly arranged or not). Alternatively the fibrous materials may be continuous filaments, woven or non-woven materials, braided materials or 3-D preforms. Such fibrous composites may include multilayer composites. Said fibrous materials are combined with the crosslinked polymer compositions in any weight fraction or volume fraction that is reasonable for the intended use. Preferably, the volume fraction fibrous material, $\Phi_{fibrous}$ is in the range $0.01 \leq \Phi_{fibrous} \leq 0.7$.

Preferred ceramic and inorganic materials include, but are not limited to, alumina, alumina silicate, bismuth titanate, boron nitride, calcium phosphate, carbon, carbon nanotubes, glass, graphite, hydroxyapatite, lead metaniobate, lead nickel niobate, lead zirconate titanate, lithium aluminate, oxide nanotubes, silicon carbide, silicone nitride, tin oxide, titanium dioxide, yttrium aluminum garnet, zirconium diboride, and combinations thereof.

Said fibrous materials may be ceramic, inorganic, metallic or polymeric. Preferred metallic fibrous materials include, but are not limited to, aluminum, copper, gold, iron, magnesium, nickel-titanium, platinum, silver, steel, alloys thereof, and combinations thereof. Preferred polymeric fibrous materials include, but are not limited to, cellulose, cellulosic derivatives (e.g., carboxymethylcellulose and hydroxyethylcellulose), chitin, chitosan, collagen, fluoropolymers, polyacrylates, polyamides, polyanhydrides, polyesteramides, polyesters, polyesterurethanes, polyetheramides, polyetheresters, polyetheresterurethanes, polymethacrylates, polyolefins, polyurethanes, polyvinylalcohol, and combinations thereof. More preferred polymeric fibrous materials include aliphatic polyamides, aliphatic polyesters, carboxymethylcellulose, chitin, chitosan, collagen, poly(ethylene terephthalate), poly(ethylene-co-propylene), poly(fluorinated ethylene-co-propylene), poly(tetrafluoroethylene-co-ethylene), poly(tetrafluoroethylene-co-hexafluoropropylene), poly(tetrafluoroethylene-co-perfluorobutyl vinyl ether), poly(tetrafluoroethylene-co-perfluoroethyl vinyl ether), poly(tetrafluoroethylene-co-perfluoromethyl vinyl ether), poly(tetrafluoroethylene-co-perfluoropropyl vinyl ether), polyetheramides, polyetheresters, polyethylene, polypropylene, polytetrafluoroethylene, polyvinylalcohol, and combinations thereof. Most preferred polymeric fibrous materials include aliphatic polyamides, aliphatic polyesters (e.g., bioabsorbable aliphatic polyesters prepared by a ring opening polymerization method such as poly(glycolide-co-trimethylene carbonate), poly(L-lactide), poly(D-lactide), poly(D,L-lactide), poly(glycolide-co-lactide) and poly(e-caprolactone)), carboxymethylcellulose, cellulose, chitin, chitosan, collagen, polyetheramides, polyetheresters, polytetrafluoroethylene (e.g., expanded polytetrafluoroethylene), polyvinylalcohol. Fibrous webs of the bioabsorbable fibers can be produced by melt-blowing or spun-bonding. Melt-blown fibrous webs are produced by entraining melt spun fibers with convergent streams of heated air to produce fine filaments.

Preferably, the other material is a self-cohering non-woven web constructed from continuous filaments of semicrystalline multicomponent polymeric systems. The self-cohering webs of U.S. Pat. No. 6,309,423 are particularly preferred.

Film-based composites may be made from the crosslinked polymer compositions themselves, or in combination with other film materials, including multilayer film laminates. Said film materials may be of the fully-dense type or of the porous type. Said film materials may be ceramic, inorganic, metallic or polymeric. Metallic film materials and polymeric film materials are preferred.

Preferred metallic film materials include aluminum, copper, gold, iron, magnesium, nickel-titanium, platinum, silver, steel, alloys thereof and combinations thereof.

Preferred polymeric film materials include fluoropolymers, polyacrylates, polyamides, polyanhydrides, polyesteramides, polyesters, polyesterurethanes, polyetheramides, polymethacrylates, polyolefins, polysiloxanes, polyurethanes, polyvinylalcohol, and combinations thereof. More preferred polymeric film materials include aliphatic polyamides, aliphatic polyesters, poly(ethylene terephthalate), poly(ethylene-co-propylene), poly(fluorinated ethylene-co-propylene), poly(tetrafluoroethylene-co-ethylene), poly(tetrafluoroethylene-co-hexafluoropropylene), poly(tetrafluoroethylene-co-perfluorobutyl vinyl ether), poly(tetrafluoroethylene-co-perfluoroethyl vinyl ether), poly(tetrafluoroethylene-co-perfluoromethyl vinyl ether), poly(tetrafluoroethylene-co-perfluoropropyl vinyl ether), polyetheramide, polyethylene, polypropylene, polysiloxanes, polytetrafluoroethylene, polyurethanes, and polyvinylalcohol. Most preferred polymeric film materials include aliphatic polyamides, aliphatic polyesters (e.g., bioabsorbable aliphatic polyesters prepared by a ring opening polymerization method such as poly(D,L-lactide), poly(D-lactide), poly(glycolide-co-lactide) and poly($\epsilon$-caprolactone), poly(glycolide-co-trimethylenecarbonate), and poly(L-lactide)), polyetheramides, polytetrafluoroethylene (e.g., expanded polytetrafluoroethylene), and polyvinylalcohol.

Said film materials are combined with the crosslinked polymer compositions in any weight fraction or volume fraction that is reasonable for the intended use. Preferably, the volume fraction film material, $\Phi_{film}$ is in the range $0.01 \leq \Phi_{film} < 0.95$.

Said film laminates may comprise one or more layers of the crosslinked polymer compositions and, optionally, one or more layers of film material. For example, a laminate may be made from an ePTFE layer and one or more crosslinked polyester compositions. The ePTFE has a microstructure of interconnected fibrils that defines pores. Preferably, the crosslinked polyester compositions has at least one transition temperature of greater than about 30° C. and less than about 100° C. and is laminated to the ePTFE layer. Preferably, at least some of the crosslinked polyester composition flows into at least some of the pores to provide attachment. Alternatively, the crosslinked polyester composition and the ePTFE may be attached via surface adhesion.

In alternative embodiments, ePTFE material may be combined with other shape memory polymer materials in accordance with the methods disclosed herein. These shape memory polymer materials include, but are not limited to the crosslinked polyester compositions described in the present application.

For example, a multi-layer film laminate may be made from three different crosslinked polyester compositions described in the present application. By choosing appropriate compositions with different transition temperatures, it is possible to provide a multi-layer film laminate that exhibits staged shape memory behavior. For example, it is possible to form a compressed laminate that may be inserted into a patient in the compressed state. Then by appropriately stimulating the laminate (e.g., heating to 37° C.), the laminate may expand in a predetermined direction by a predetermined amount. In some patients, this degree of expansion may be appropriate, and in others additional expansion may be desirable. In the latter group of patients, the laminate may be again stimulated to invoke a shape memory reaction in one or more of the remaining layers. For example, this might be achieved by heating the laminate to 45° C., and to cause additional expansion of the laminate material. By incorporating additional layers of the crosslinked polymer compositions on the film laminates, it is possible to produce a composite material which exhibits two, three, four or more stages of controlled shape memory behavior. Alternatively, the composite may be stimulated to move in a first direction by a first trigger and then stimulated to move in a second direction (e.g., opposite the first direction) by a second trigger.

Said crosslinked polymer compositions may function to bond film materials to one another to form a multilayer film laminate article comprising the crosslinked polymer compositions.

Alternatively, the other materials in the composite are microporous membranes include, but are not limited to, cellulosics, chlorinated polymers, fluorinated polymers, poly (tetrafluoroethylene-co-ethylene), poly(tetrafluoroethylene-co-hexafluoropropylene), poly(tetrafluoroethylene-co-perfluorobutyl vinyl ether), poly(tetrafluoroethylene-co-perfluoroethyl vinyl ether), poly(tetrafluoroethylene-co-perfluoromethyl vinyl ether), poly(tetrafluoroethylene-co-perfluoropropyl vinyl ether), polyamides, polycarbonates, polyolefins and combinations thereof. A most preferred material is expanded porous polytetrafluoroethylene (PTFE) made in accordance with the teachings of U.S. Pat. No. 3,593,566 herein incorporated by reference. This material is commercially available in a variety of forms from W. L. Gore & Associates, Inc., of Elkton, Md. Such membranes preferably have a thickness from about 5 μm to up to 1.0 mm, a porosity of greater than 10%, and a pore diameter less than 10 microns.

Where an expanded PTFE membrane is used, the preferred thickness is at most about 1.0 mm and most preferably between 5 μm and 0.019 mm, the preferred porosity is between 20-98% and most preferably is between 70-95%, and the preferred pore diameter is between 0.05 μm and 5 μm, and most preferably is about 0.2 μm.

Other composites are formed by combining the crosslinked polymer compositions with particulates (e.g., a filled polymer). Such particulates may be chosen to improve acoustic, dimensional stability, electrical, frictional wear, lubrication, magnetic, processability, strength, toughness properties. The particulates may be in various forms, including, but not limited to, aggregates, blocks, cubes, fibers, flakes, spheres, tubes and combinations thereof. Particulate materials include, but are not limited to, beidellite, bentonite, biodegradable polymeric particles (e.g., polydioxanone, polyglycolic acid, polyglycolide, polylactic acid, polylactide, and copolymers of glycolic acid or glycolide and either lactic acid, lactide or trimethylene carbonate), calcite, carbon, carbon black, ceramics (e.g., alumina and layered aluminate oxides), glass (e.g., spheres or fibers), hectorite, hydrotalcite, illite, kaolinite, mica, montmorillonite, nontronite, saponite, sauconite, sepiolite, stevensite, talc, vermiculite and combinations thereof. Preferably, the particulates are biocompatible particulates, and more preferably are bioabsorbable. Such particulate based composites may be useful for nano-composite materials.

Optionally, the composite membrane may be reinforced with a woven or non-woven material joined to the other material. Suitable woven materials include for example, scrims made of woven fibers of expanded porous polytetrafluoroethylene, commercially available from W. L. Gore & Associates, Inc., of Elkton, Md.; webs made of extruded or oriented polypropylene netting commercially available from Conwed, Inc. of Minneapolis, Minn.; and woven materials of polypropylene and polyester of Tetko Inc., of Briarcliff Manor, N.Y. Suitable non-woven materials include for example, a spun-bonded polypropylene or polyester.

For example, a polypropylene woven fabric may be laminated to the other material by any conventional technique, including, but not limited to, hot roll lamination, ultrasonic lamination, adhesive lamination, forced hot air lamination and other techniques so long as the technique does not damage the integrity of the other material. Preferably, such lamination is achieved before the other materials are combined with the crosslinked polymer compositions. The support structure may aid in processing and/or provide improved mechanical properties to the final composite.

The composites may be formed by imbibing within the voids or pores of the other materials an intermediate polymer composition obtained from a first polymerization stage of the two-stage manufacturing process described above. Preferably, the intermediate polymer composition substantially imbibes into the other materials to fill the voids or pores. Alternatively, only some of the voids may be filled or all of the voids may be partially filled. In another alternative, the other material may be coated with crosslinked polymer compositions, or the crosslinked polymer compositions can be cast as a sheet, and laminated to another material. In yet another alternative, the hydroxyl or carboxylic acid groups of the crosslinked polyester may be conjugated with moieties of the other materials. Combinations of these embodiments are possible.

In one embodiment, the intermediate polymer is dissolved in a solvent to form an intermediate solution before imbibing. The resulting intermediate solution is applied to the other material so as to imbibe and occlude the voids or pores of the other material. Solvents that may be suitable for use include, but are not limited to, acetone and methyl ethyl ketone.

The solution may be applied to the membrane by any conventional coating technique including, but not limited to, forward roll coating, reverse roll coating, gravure coating, doctor coating, kiss coating, dipping, brushing, painting, and spraying so long as the liquid solution is able to penetrate the voids of the other material. Excess solution from the surface of the other material may be removed. After treatment, the other material is dried either at room temperature or at an elevated temperature. Oven temperatures may range from 60-200° C., preferably 120-160° C. Preferably, this treatment step is repeated until voids of the other material are completely filled.

The actual number of treatments necessary to achieve a predetermined degree of filling is dependent on the thickness and porosity of the other material. Preferably, the solution is applied to the other material with between 1 and 8 treatments. Optionally, both sides of the other material may be treated simultaneously thereby reducing the number of treatments required.

Alternatively, hot melt processes may be used to flow the intermediate polymer at least partially into the pores of the other materials. For example, an intermediate reaction product (discussed above) is formed from a diol, a triol and a diacid, and that intermediate reaction product is heated, preferably to a temperature at which the melt viscosity is greater than about 0.01 poise and less than about 1,000 poise, combined with a porous substrate material such that the intermediate reaction product is disposed within at least some of the pores of the substrate, and then the resulting composite is cooled. Melt viscosity may be determined by standard techniques, such as parallel plate or cone and plate techniques.

Regardless of the method of imbibing and once the pores of the other materials are filled sufficiently with the intermediate polymer, polymerization preferably is continued to achieve a desired residual acidity. Preferably, the residual acidity is in the range of greater than about 0.0001 meq. acid/gram to less than about 1.0 meq. acid/gram. The composite material preferably is heated under vacuum or inert gas during such polymerization. It also is possible to react the inventive reaction compositions with the other materials.

Medical devices disclosed herein may comprise either the crosslinked polymer compositions described herein (having shape memory or not) or other shape memory materials. The crosslinked polymeric materials may be used in combination with other materials (including, but not limited to other polymeric, metallic, inorganic and ceramic materials) to form composites useful in medical devices. These materials or composites may be porous materials or foams or not.

Medical devices may incorporate a polyester composition that does not have shape memory properties. For example, the polymer compositions described herein may be used in hemostatic plugs as described below.

Alternatively, the medical devices described herein may utilize shape memory behavior. In this aspect, such medical devices have at least one component having an undeployed shape and a deployed shape, corresponding to a metastable state and a original or stored state of the shape memory polymer, respectively. Such medical devices may utilize the transition from the metastable state to the original state. Stimulation of the shape memory property causes deployment of the component by initiating a transition in the shape memory material from the metastable state to the original state. The transition may be stimulated by any stimulus, such as the stimuli described above including, but not limited to, light, heat, radiation or other.

Where the stimulus is heat, the shape memory component is deployed by heating to a temperature and for a time sufficient to melt a crystalline or semi-crystalline phase of the shape memory material.

Medical devices utilizing heat as a stimulus are prepared by heating the shape memory component (in its deployed shape) to a temperature and for a time sufficient to melt a crystalline or semi-crystalline phase of the shape memory material. While heated, the shape memory component is deformed from the deployed shape to an undeployed shape. The component then is cooled. During this cooling, a crystalline or semi-crystalline phase of the shape memory material forms. Preferably, this cooling is to room temperature. Because the crystalline or semi-crystalline phase is formed, the shape memory component is fixed in the undeployed shape. It is intended that the shape memory component will retain this undeployed shape at room temperature indefinitely (metastable state), and will be capable of reverting to the original or deployed shape upon application heating to a temperature and for a time sufficient to melt a crystalline or semicrystalline phase of the shape memory material.

Figure 7:
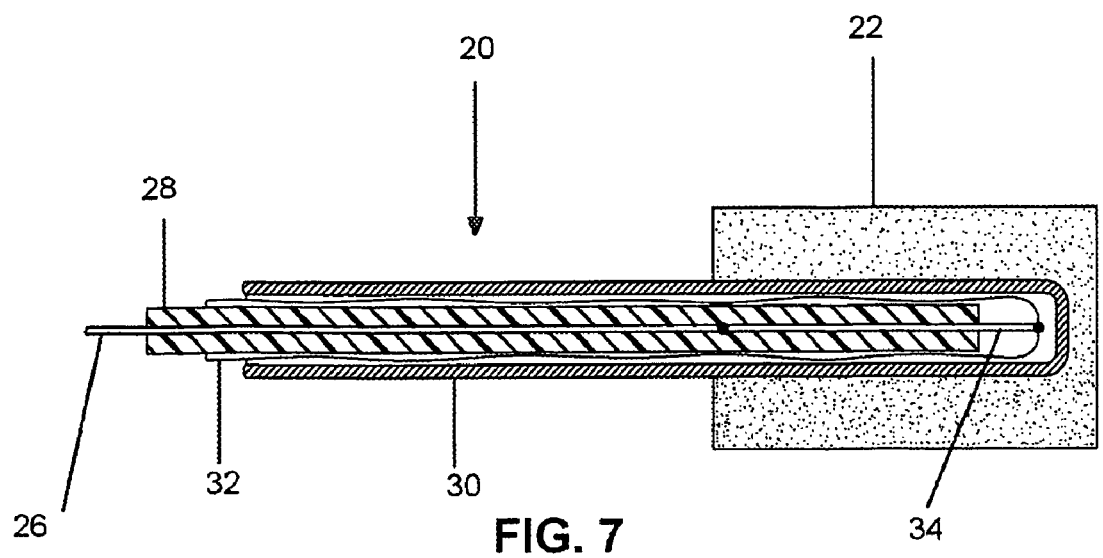
FIG. 7 is a longitudinal cross-sectional view of an exemplary aneurysm repair device.
Figure 8:
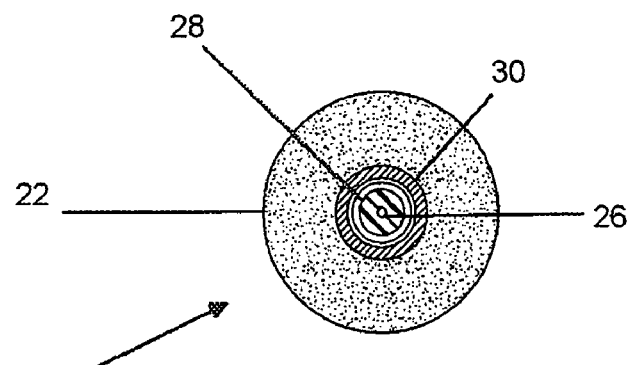
FIG. 8 is an axial cross-sectional view of an exemplary aneurysm repair device.
Figure 9:
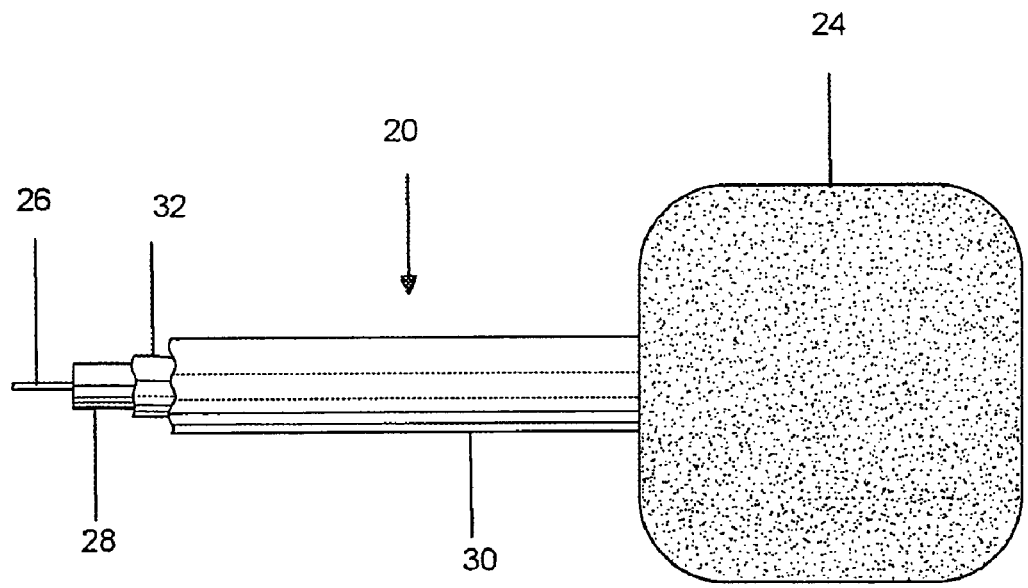
FIG. 9 is a schematic representation of an exemplary aneurysm repair device after expansion of the foam crosslinked polymer composition.
Figure 10:
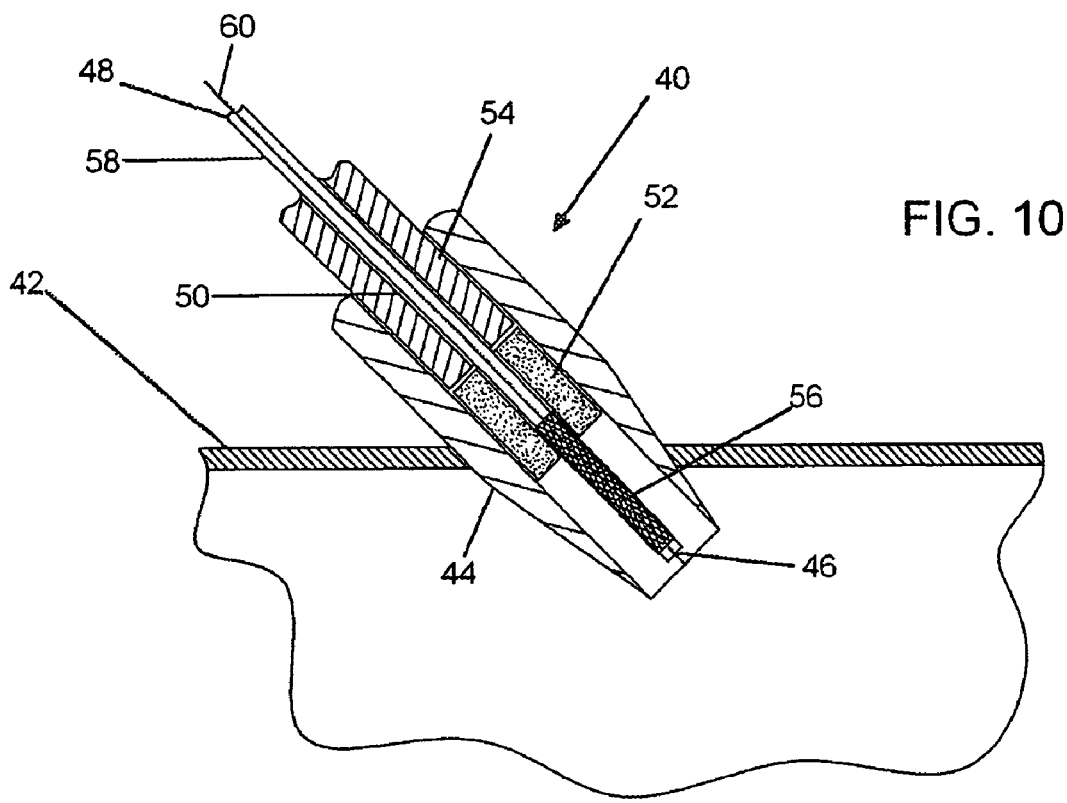
FIG. 10 is a schematic representation of an exemplary intraluminal delivery device during introduction into the lumen.

One such exemplary medical device is an aneurysm repair device (20) that is shown in FIGS. 7-9. Such devices may be used to deliver a shape memory component in a compressed undeployed shape, and then selectively deployed once it has been placed within the aneurysmal sac to fill the aneurysmal sac.

Aneurysm repair device (20) has a shape memory component (22), which can be made using any of the materials discussed herein. Advantageously, the shape memory component (22) is foam (22). In an alternative embodiment, the aneurysm repair device (20) has a foam component (22) that does not exhibit shape memory behavior, but rather mechanically expands.

Preferably, the compression reduces at least one dimension of the foam by at least 50%, more preferably by at least 70% and most preferably by at least 75% of the like dimension of the deployed shape. The foam then is cooled to room temperature. This provides a metastable compressed foam.

The compressed foam then is releasably affixed to an actuator, which is configured to selectively stimulate the foam to change from the metastable state to the original state thereby deploying the device. In FIG. 7, this actuator is based on resistive heating. An electrically conductive wire (26) is at least partially covered with insulation (28).

The insulated wire (26, 28) then is disposed within a shield conductor (32), which in turn is disposed within an insulation cover (30). At the distal end, closest to the foam (22), the actuator is provided with a resistive element (34). Preferably, each of the elements of the actuator is biocompatible.

It should be understood that, alternative means for stimulating the metastable compressed foam (22) are possible. For example, instead of resistive heating, an optical fiber may be used and laser light may be directed on the metastable compressed foam (22) to stimulate its shape memory behavior. In such an embodiment, it may be advantageous to include a dye in the metastable compressed foam (22) to facilitate shape memory behavior.

In use, the aneurysm repair device (20) is delivered endovasularly to the site of the aneurysm. It then is positioned within the aneurysm. Once the shape memory material (22) is properly placed, electrical power is applied to the electrically conductive wire (26). This, in turn, causes heating of the resistive element (34). The shape memory material (22) is heated above its transition temperature by the resistive element (34), and the shape memory material (22) exhibits shape memory behavior, and expands to its original state (24) as shown in FIG. 9. In so doing, it is intended that the expanded shape memory material (24) will fill and occlude the aneurysmal sac. Thereafter, the actuator is removed from the expanded shape memory material (24) and is withdrawn from the patient.

Another exemplary medical device is an intraluminal delivery device (40) that is shown in FIGS. 10-14. Such an intraluminal delivery device (40) is intended to permit repair of openings in a lumen, particularly in the vasculature (e.g., femoral artery). Such openings are frequently formed to permit introduction of medical device(s) for medical procedures, e.g., endovascular procedures to treat aneurysms, cerebral vascular malformations, and arteries that have been occluded by plaque. For example, shape memory foam may be used to repair a vascular access wound that results from the introduction and removal of a device used in a minimally invasive surgical procedure. The foams may be manipulated, formed and delivered in such a way to act as vascular closure devices that take advantage of the hemostatic properties shown in the examples below.

Broadly speaking, such a device includes an introducer (44), and a vascular closure assembly (45). Introducers are well known in the art. In the embodiment depicted in FIGS. 10-13, the introducer (44) is a sheath defining a central lumen.

A vascular closure assembly (45) (depicted in FIG. 13) is within the introducer (44), and has a distal end (46) and a proximal end (48). In the embodiment depicted in FIGS. 10-14, the vascular closure assembly (45) has a shaft member (50), a shape memory member (52) and a pusher (54). The introducer (44), the shaft member (50), the shape memory member (52) and the pusher (54) are movable independently with respect to one another.

The shaft member (50) extends between the distal and proximal ends, and has an expandable portion (56) capable of being selectively deformed between a retracted position and an expanded position. The expandable portion (56) is near the distal end (46).

The shaft member (50) may, for example, be made from braided nitinol wire. A non-expandable portion (58) of the shaft member (50) may be made by substantially covering the braided shaft with a polymeric material, which prevents radial expansion, elongation or shortening of the braid in that portion. Alternatively, expansion of the braided shaft also may be restricted by applying the polymeric material along a portion of the inner lumen of the braided shaft. Likewise, materials other than polymeric materials may be used for this purpose.

An actuating wire (60) is disposed within the shaft member (50) and is attached to the distal end (46).

It should be understood that the shaft member may be made from various other biocompatible materials (e.g., stainless steel), so long as the material is capable of being selectively deformed between the retracted and expanded positions. Likewise, the shaft member may be constructed without braiding using other manufacturing techniques including, but not limited to, adhering (e.g., biocompatible adhesives), fusion welding, laser cutting, laser welding, soldering, and combinations thereof.

The shape memory member (52) of the vascular closure assembly (45) may be made of any of the materials discussed above so long as it exhibits shape memory behavior. Preferably, the shape memory member (52) is bioabsorbable. In the embodiment depicted in FIGS. 10-14, the shape member is compressed shape memory foam plug (52) disposed around the shaft member (50).

The pusher (54) also is disposed within the introducer (44) and is proximal to the foam plug (52). In the embodiment depicted in FIGS. 10-14, the pusher (14) surrounds a proximal portion of the shaft member (50).

The intraluminal delivery device may be used as follows. First, the introducer (44) is inserted into a lumen (42). Typically, a needle (not depicted) is first inserted into a lumen (42). Then, a guide wire (not depicted) is placed through the needle into the lumen. The needle then is removed. An introducer (44) is placed over the guide wire and into the lumen (42).

Insertion of the introducer (44) creates an opening in the lumen (42). Various medical device(s) (not depicted) may be delivered into the patient via the introducer (44). Once the medical procedures are completed, the vascular closure assembly (45) is delivered to the repair site via the introducer (44) and preferably over the pre-existing guide wire (not depicted).

Figure 11:
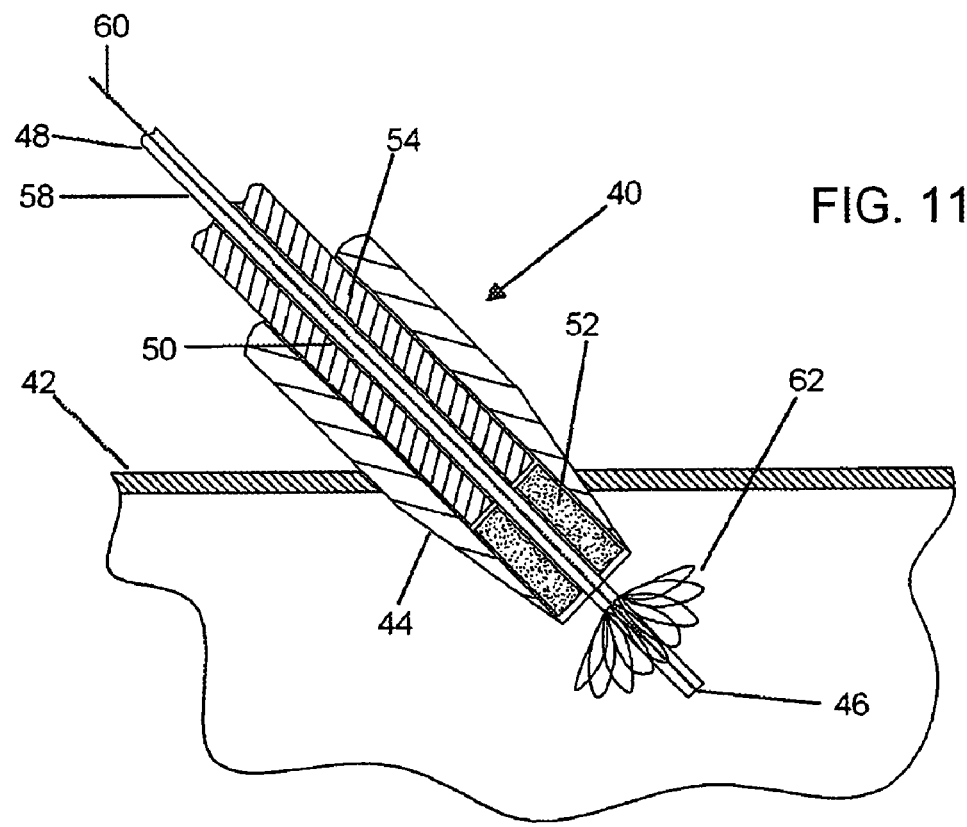
FIG. 11 is a schematic representation of an exemplary intraluminal delivery device after expansion of part of the shaft member.

The expandable portion (56) of the shaft member (50) is positioned beyond the repair site. Then the expandable portion (56) is expanded by holding the proximal end (48) of the vascular closure assembly (45), and pulling the actuating wire (60) proximally. This causes the distal end (46) of the vascular closure assembly (45) to move proximally, and the expandable portion (56) to expand within the unrestrained portion to form a projection (62) extending perpendicularly to a longitudinal axis of the device as shown in FIG. 11.

Figure 12:
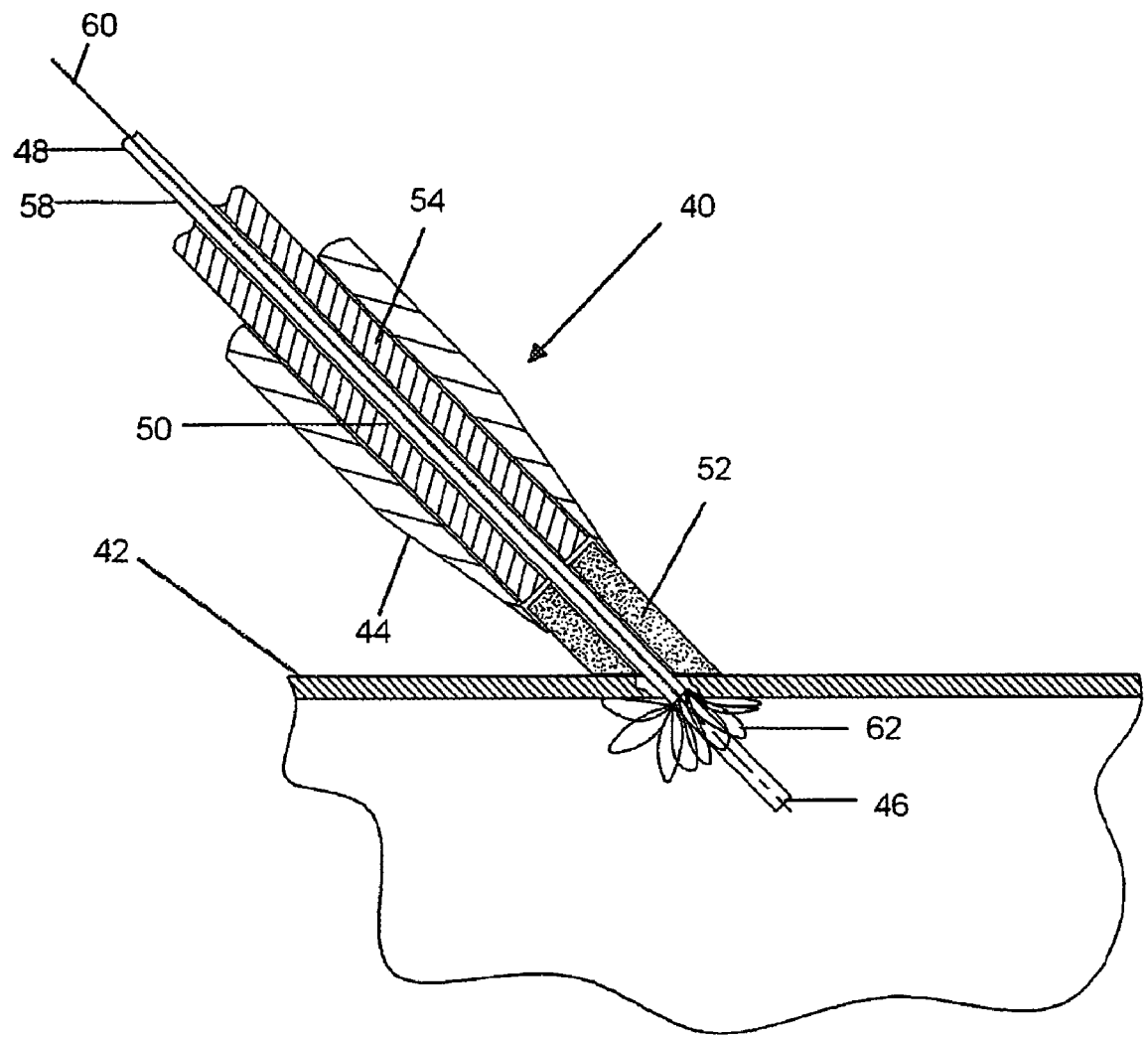
FIG. 12 is a schematic representation of an exemplary intraluminal delivery device as the introducer is removed.

Next, the pusher (54) and the plug (52) are pushed distally against the projection (62). With the plug (52) locked between the pusher (54) and the projection (62), the vascular closure assembly (45) is withdrawn proximally until the projection (62) contacts an inner surface of the lumen (42) as shown in FIG. 12.

Figure 13:
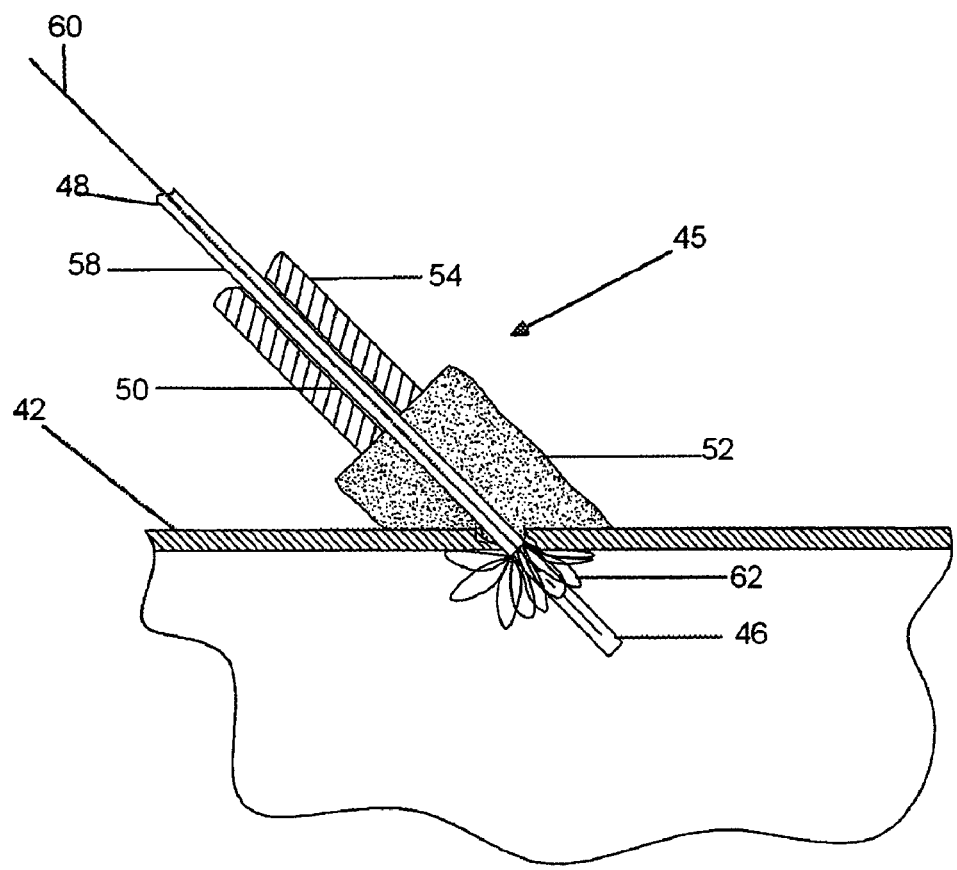
FIG. 13 is a schematic representation of an exemplary intraluminal delivery device after the introducer is removed and the plug expands.
Figure 14:
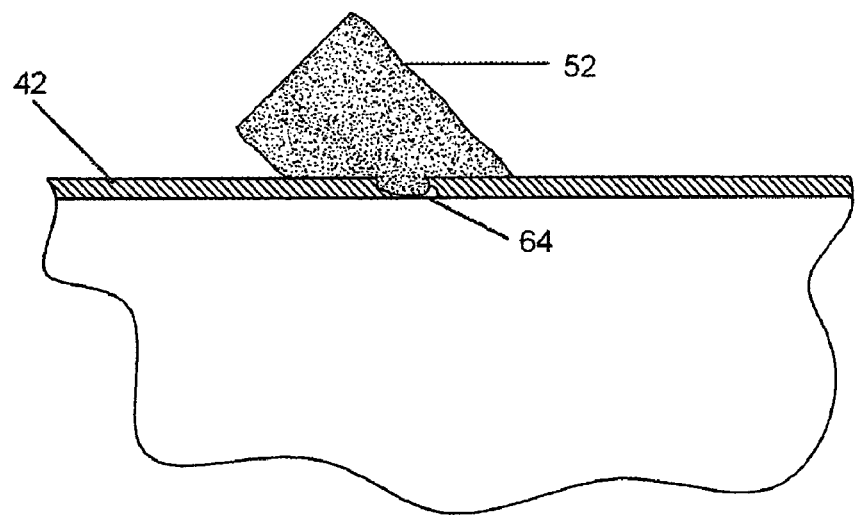
FIG. 14 is a schematic representation of an exemplary intraluminal delivery device after the shaft member is removed.

The shape memory property of the plug (52) is activated either by body heat or a stimulus (e.g., via warm saline solution provided through the introducer). The stimulus causes the deployment of the plug (i.e., invokes transition from the metastable state to its original state). The introducer (44) then is withdrawn. See FIGS. 12-13. The unrestricted plug (52) then expands to patch the opening of the lumen (42) as can be seen in FIGS. 13 and 14. The plug (52) is disposed against an outer surface of the lumen (42). In some embodiments, a portion of the polymeric foam also may be disposed within a hole (64) created by the introducer (44) as shown in FIG. 14; however this may not be necessary for an effective repair.

After placing the plug (52), the expandable portion (56) is retracted by pushing the actuating wire (60) distally. The shaft member (50) may be withdrawn while the plug (52) is held in place by the pusher (54), which is ultimately removed.

Figure 15:
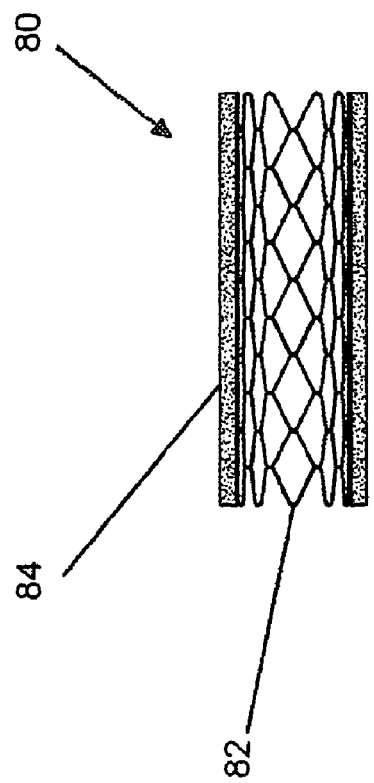
FIG. 15 is a schematic representation of an exemplary deployment means for an endoluminal device in an expanded or deployed shape.
Figure 16:
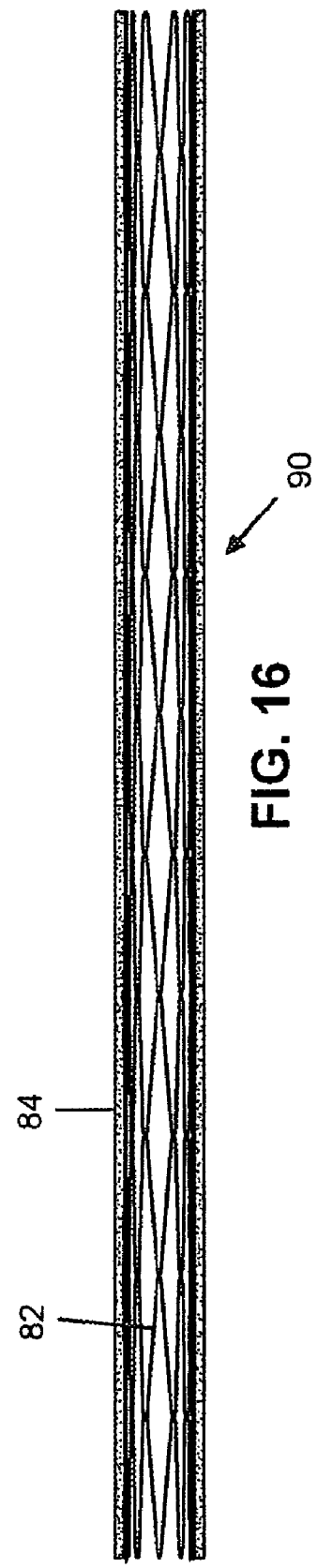
FIG. 16 is a schematic representation of an exemplary deployment means for an endoluminal device in reduced or undeployed shape.

Another exemplary medical device is a deployment means (80) for an endoluminal device, e.g., a stent that is shown in FIGS. 15-16. Other illustrative endoluminal devices include, but are not limited to, endoluminal prostheses, stent-grafts, vena-cava filters, and the like. The stent (82) may or may not be made of a shape memory alloy.

A shape memory material or a shape memory prepolymer (84) is applied to the braided stent (82). The shape memory material (84) may be any of the materials discussed herein so long as it exhibits shape memory behavior. For example, the shape memory material (84) may be a composite material, e.g., a composite material including a crosslinked polymer composition exhibiting shape memory behavior, as well as another material. In one preferred embodiment, the shape memory material (84) is bioabsorbable. In another preferred embodiment, the shape memory material (84) is a composite including a crosslinked polymer composition and an ePTFE nonwoven web.

An exemplary method of manufacturing a deployment means is now described. First, the stent (82) is formed. As shown in the depicted embodiment, a nitinol wire is braided into a generally tubular construct on a mandrel. Alternatively, the stent may be constructed using other known materials and techniques including, but not limited to adhering (e.g., biocompatible adhesives), fusion welding, laser cutting, laser welding, soldering. A further alternative is to manufacture the stent from a sheet or cannula, e.g., using a laser.

The second step is to apply the shape memory material (84) to the stent (82). For example, the shape memory material (84) may be continuously wrapped in a machine direction around an exterior surface of the braided stent (82). The assembly then is heated to relatively high temperatures (e.g., 160° C.) for an extended period (e.g., 10 hours). After cooling to room temperature, the assembly including the stent (82) and the applied shape memory material (84) may be removed from the mandrel. The deployment means is in an expanded or deployed shape (1) as shown in FIG. 15. This corresponds to the original state of the shape memory composite.

The third step is to change the profile of the deployment means. The deployment means (80) is heated to a temperature and for a time period sufficient to melt a crystalline or semi-crystalline phase of the shape memory material and axially stretched, for example by grabbing and pulling the two opposing ends of the nitinol braid (82). This axial stretching causes the diameter of the deployment means to be reduced and the overall length of the deployment means to be increased. The deployment means is in an undeployed shape in FIG. 16. The deployment means (90) then is cooled. After being fixed in an undeployed shape (metastable state), the deployment means is placed on a delivery catheter.

A deployment means may be used as follows. Typically, a needle is first inserted into a blood vessel. Then, a guide wire is placed through the needle into the blood vessel. The needle then is removed. An introducer is placed over the guide wire and into the blood vessel. Next, the delivery catheter with the deployment means is advanced through the introducer over a guide wire and into the blood vessel. The catheter then is guided to the desired location within the vasculature (e.g., aorta) and the guide wire is removed.

The deployment means then is stimulated to cause the deployment means to revert to its deployed shape, i.e., the deployment means shortens in length and expands in diameter, and preferably substantially recovers its original dimensions. For example, the deployment means is heated to a predetermined temperature, i.e., a transition temperature of the shape memory material (84). This heating may be accomplished by the patient's own body heat, warm saline provided via the introducer, etc.

The aliphatic crosslinked polyester and composites made therefrom are extremely well-suited for various applications, particularly those benefiting from biocompatibility, bioabsorbability, shape memory behavior or combinations thereof. Illustrative examples of medical applications include, but are not limited to bandages, bone pins, drug delivery devices, grafts, hemostatic devices, stents, surgical reinforcement, sutures, vascular closure devices, and the like. Non-medical applications include, but are not limited to packaging and food preparation and other uses where disposability is of concern.

The following examples are intended to demonstrate, but not to limit, the invention(s) described herein, and methods of making them.

EXAMPLE 1

A crosslinked polymerization reaction product of a diacid, diol and a triol was made following a two stage method. In the first stage, the following components were placed into a 500 ml glass reactor: The diacid component was 202.25 grams sebacic acid (Aldrich, 99%), the diol was 43.46 grams ethylene glycol (Aldrich, 99.8% anhydrous), and the triol was glycerol in the amount of 26.26 grams (Aldrich, 99.5%+ spectrophotometric grade). The reactor was equipped with agitation, heating, vapor condensing, liquid volume measuring, temperature regulating, temperature measuring and nitrogen gas purging capabilities.

Figure 17:
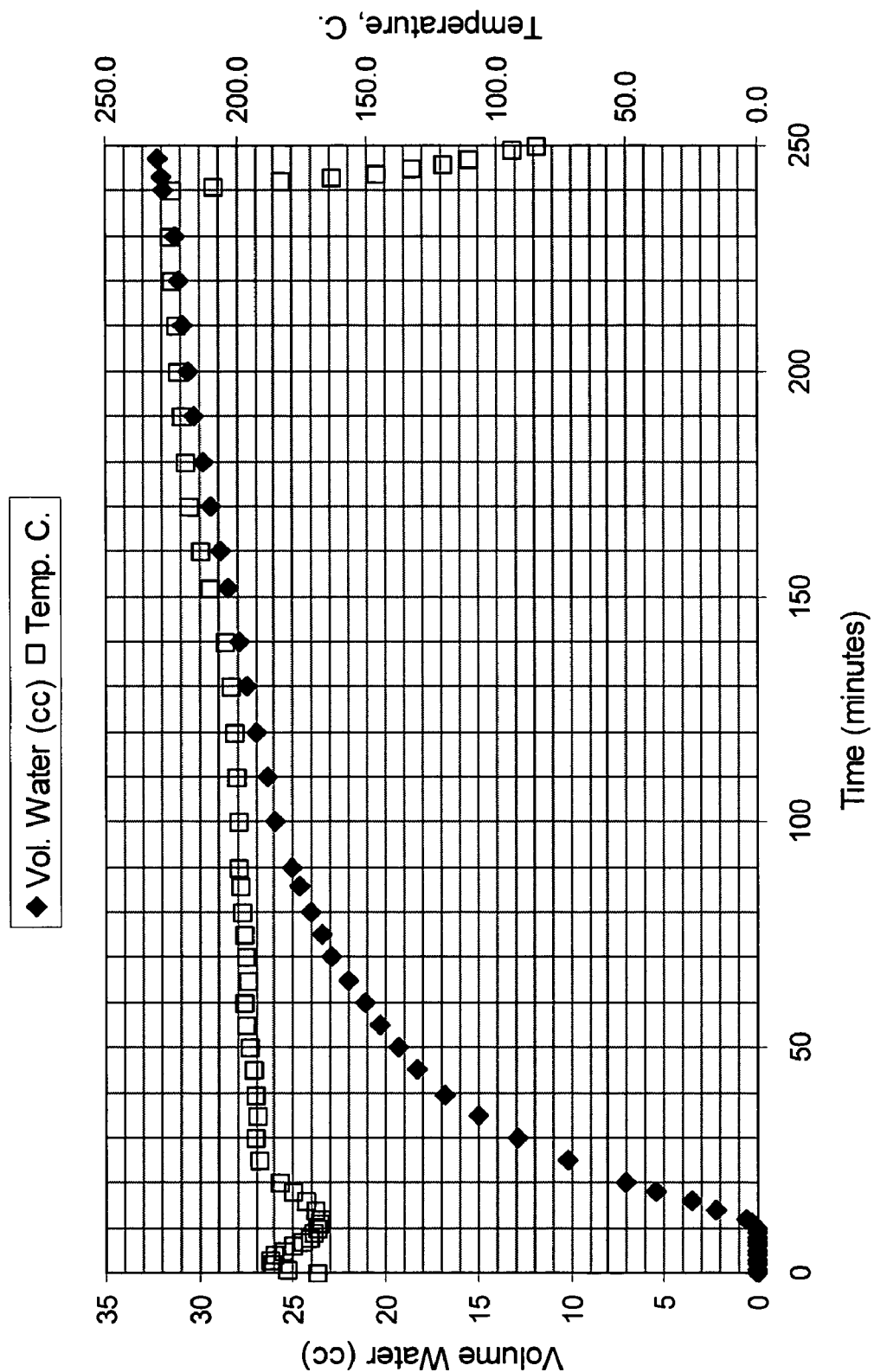
FIG. 17 is a temperature and water evolution history for the polymerization reaction of Example 1.

At room temperature the reactants formed a heterogeneous mixture of solid and liquid phase. As temperature was increased to about 170° C., the mixture became a homogeneous liquid. Time and process parameters were recorded when all material was a single phase liquid. Byproduct water vapor evolving from the reactor was condensed and collected in a volumetric receiving tube graduated in 0.1 cc increments. The temperature and water evolution history is shown in FIG. 17. A total of 32.2 cc byproduct water was collected.

237 grams of white waxy intermediate reaction product, corresponding to 98.9% of the theoretical yield, was produced in the first stage of polymerization. The product was titrated with potassium hydroxide (KOH). Titration reflected a residual acidity of 0.8049 meq. acid/gram. The product was soluble in acetone at room temperature.

In the second stage, 9.05 grams of the intermediate reaction product (prepared as described above) was placed into each of four 125 mm diameter Teflon™ molds at 22° C. The Teflon™ molds containing the intermediate were placed in a vacuum oven with the temperature set at 130° C. The pressure was initially set at atmospheric pressure. The intermediate reaction product melted to form a clear viscous liquid within five minutes. A vacuum was applied to remove trapped gases and volatiles from the sample. After 2 hours and 25 minutes, pressure was raised to atmospheric with nitrogen gas at a constant flow rate of approximately 180 cc/min. The liquid samples were removed from the oven and redistributed evenly over the entire Teflon™ mold bottom surface by gently "rocking" the Teflon™ mold. The nitrogen gas flow rate and temperature were maintained at approximately 180 cc/min and polymerization continued at 130° C. for 3,900 minutes. The nitrogen gas flow then was terminated and pressure was again reduced. Polymerization continued for 4,320 minutes under these conditions. The temperature was decreased to ambient over several hours. After increasing pressure to atmospheric, the product was removed from the Teflon™ mold to yield four 125 mm diameter disks that were approximately 1 mm thick.

Figure 18:
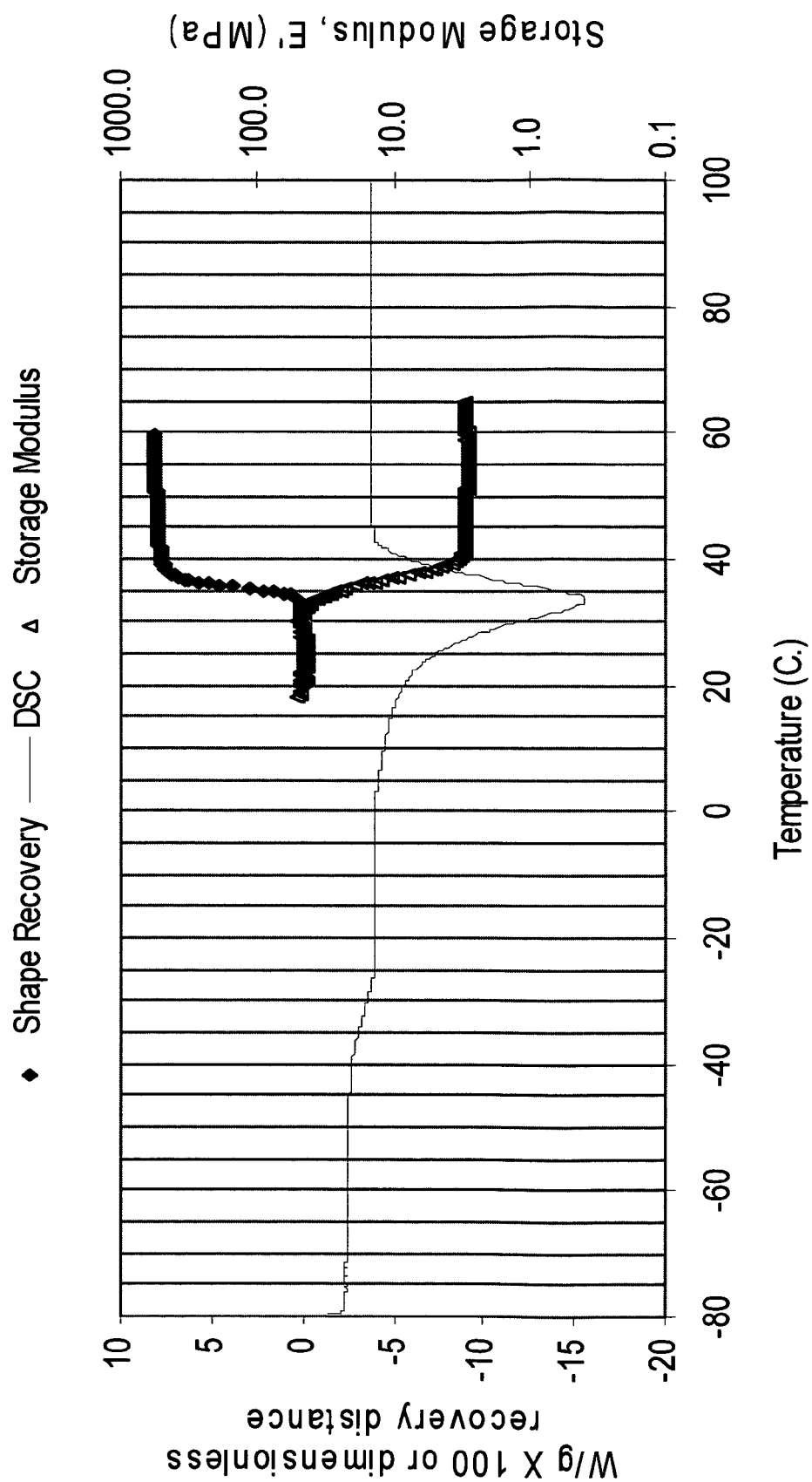
FIG. 18 are results of differential scanning calorimetry (DSC), mechanical and shape recovery experiments for the reaction product of Example 1.

The product was not soluble in acetone, but swelled in acetone. Upon cooling to 23° C., the product was not optically clear. Titration reflected residual acidity of 0.0671 meq. acid/gram. The final product exhibited shape memory behavior when exposed to a temperature of between 35° C. and 39° C. during the shape memory testing procedure described herein. The Young's modulus, E', was 48 MPa at 22° C. and 9.0 MPa at 37° C. Results of differential scanning calorimetry (DSC), mechanical and shape recovery experiments are shown in FIG. 18. The glass transition temperature, $T_g$, was found to be about −37° C. upon heating from −80° C. at 2° C./min.

When tested in accordance with the cytotoxicity testing described herein, the final product was found to be nontoxic-grade 1 to mammalian cells.

The material of example 1 was tested in vivo. Samples were surgically implanted in longissimus dorsi muscle of New Zealand White rabbits. The procedure of ISO 10933: Part 6 was followed. Prior to implantation, the material was sterilized by gamma radiation at 16-18 kGy. After implantation for 45 days, the muscle was surgically removed and fixed in 10% neutral buffered FORMALIN®. The muscle was sectioned, stained and examined microscopically. No histological evidence of adverse tissue reaction was found at any of the implant sites, suggesting the material was biocompatible. No evidence of the implants was found.

COMPARATIVE EXAMPLE 2

202.25 grams sebacic acid and 62.07 grams ethylene glycol were combined in a 500 ml glass reactor. The reactor was equipped with agitation, heating, vapor condensing, liquid volume measuring, temperature regulating, temperature measuring and nitrogen gas purging capabilities. At room temperature, the reactants formed a heterogeneous mixture of solid and liquid phase. As temperature was increased to about 145° C., the mixture became a homogeneous liquid. Time and process parameters were recorded when all material was a single phase liquid. Byproduct water vapor evolving from the reactor was condensed and collected as described in Example 1. Total byproduct water was 32.9 cc.

227 grams of the white brittle intermediate reaction product, corresponding to 98.1% of the theoretical yield, were produced. Titration reflected a residual acidity of 0.7119 meq. acid/gram. The product was partially soluble in acetone at 22° C., and slightly more so at 50° C., and was completely soluble in dimethyl sulfoxide at 70° C. and completely soluble in hexaflouorispropanol (HFIP) at 22° C.

A 125 mm diameter Teflon™ mold was charged with 25.6 grams of the intermediate reaction product prepared as described above. The mold containing the intermediate was placed in a vacuum oven with the temperature set at 126° C. The pressure was initially set at atmospheric pressure. The solid intermediate melted to form a clear viscous liquid within ten minutes. Temperature was maintained at 125° C. and pressure reduced. After 4,320 minutes, oven pressure was raised to atmospheric and cooled to ambient temperature over several hours.

Upon cooling the product was not optically clear. The product was partially soluble in acetone at 50° C., but less so than the intermediate reaction product described above in this Example. The product was completely soluble in dimethyl sulfoxide at 70° C. and in HFIP at 22° C. Titration reflected a residual acidity of 0.4563 meq. acid/gram. The final product did not exhibit shape memory behavior.

The final product was brittle and no mechanical properties could be evaluated at 22° C. or at 37° C. Upon heating to a temperature above the product's melting point, the product transformed to a viscous fluid.

COMPARATIVE EXAMPLE 3

202.25 grams sebacic acid and 92.09 grams glycerol were combined in a 500 ml glass reactor. The reactor was equipped with agitation, heating, vapor condensing, liquid volume measuring, temperature regulating, temperature measuring and nitrogen gas purging capabilities.

At room temperature the reactants formed a heterogeneous mixture of solid and liquid phase. As temperature was increased to about 153° C., the mixture became a homogeneous liquid. Time and process parameters were recorded when all material was a single phase liquid. Byproduct water vapor evolving from the reactor was condensed and collected as described in previous examples. A total of 31.6 cc water was collected.

259 grams of the solid product were recovered corresponding to 98.6% of the theoretical yield. Upon cooling to ambient temperature, the product formed an optically clear, very tacky viscous fluid. The product was further cooled using dry ice and formed a solid that was not optically clear. The intermediate reaction product was completely soluble in acetone. Titration reflected a residual acidity of 0.764 meq. acid/gram.

A 125 mm diameter Teflon™ crystallizing dish was charged with 25.5 grams of the intermediate reaction product prepared as described above. This was placed in a vacuum oven with the temperature set at 126° C. The pressure was initially set at atmospheric pressure. A decrease in the viscosity of the product was observed. After 10 minutes, pressure was reduced and temperature of 125° C. was maintained for 4,320 minutes. The temperature then was decreased to ambient over three hours and pressure was raised to atmospheric. The final product was removed from the Teflon™ mold to yield a 125 mm diameter disk that was approximately 2 mm thick.

Upon cooling, the final product was optically clear. It was not soluble in acetone, but swelled in acetone. Titration yielded a residual acidity of 0.058 meq. acid/gram.

The final product did not exhibit shape memory behavior when subjected to the shape memory test procedure described herein. The Young's modulus, E', was 2.1 MPa at 22° C. and 2.1 MPa at 37° C.

EXAMPLE 4

67.3 grams of the intermediate prepared and described in Comparative Example 2 and 32.7 grams of the intermediate prepared and described in Comparative Example 3 were combined in a 4 ounce glass jar, and placed in a vacuum oven at 125° C. and atmospheric pressure. A 125 mm diameter Teflon™ crystallizing dish and a laboratory mixing propeller assembly also were placed in the oven at this time. After three hours, the glass jar and its liquid intermediate contents were removed from the oven and immediately placed in an appropriate sized heating mantle, a thermocouple inserted into the molten mass and the temperature maintained at 125±5° C. for five minutes. The intermediates then were mixed at moderate speed for five minutes until they appeared thoroughly mixed and formed a visibly homogeneous single-phase liquid. 25 grams of the liquid was transferred to the preheated Teflon™ crystallizing dish, and placed back in the vacuum oven at 125° C. and atmospheric pressure. The pressure was reduced and polymerization continued for 4,260 minutes. Then the pressure was increased to atmospheric and the mold and polymer removed from the oven and placed on a laboratory benchtop at 22° C. to cool. After one hour, it was removed from the mold yielding a disk of approximately 2 mm thickness.

Upon cooling, the product was not optically clear. The product swelled in acetone at 50° C., swelled in HFIP at 22° C. and swelled in dimethyl sulfoxide at 70° C. Titration reflected a residual acidity of 0.2293 meq. acid/gram. The product exhibited shape memory behavior when exposed to a temperature of between 60° C. and 66° C. during the shape memory testing procedure described herein. The Young's modulus, E', was 278 MPa at 22° C. and 160 MPa at 37° C. When tested in accordance with the cytotoxicity testing described herein the product was nontoxic grade 0 to mammalian cells.

EXAMPLE 5

46.8 grams of the intermediate prepared and described in Comparative Example 2 and 53.2 grams of the intermediate prepared and described in Comparative Example 3 were combined in a 4 ounce glass jar.

The glass jar containing these intermediates was placed in a vacuum oven at 125° C. and atmospheric pressure. A 125 mm diameter Teflon™ crystallizing dish and a laboratory mixing propeller assembly also were placed in the oven at this time. After three hours, the glass jar and its liquid intermediate contents was removed from the oven and immediately placed in an appropriate sized heating mantle, a thermocouple inserted into the molten mass and the temperature maintained at 125±5° C. for five minutes. The intermediates then were mixed at moderate speed for five minutes until the intermediates appeared thoroughly mixed and formed a visibly homogeneous single-phase liquid. 25 grams of the liquid was transferred to the preheated Teflon™ crystallizing dish, and placed back in the vacuum oven at 125° C. and atmospheric pressure. The pressure was reduced, and polymerization continued for 4,260 minutes. Then the pressure was increased to atmospheric and the mold and polymer removed from the oven and placed on a laboratory benchtop at 22° C. to cool.

While cooling, the product was not optically clear. After one hour it was removed from the mold yielding a disk of nominally 2 mm thickness. The product swelled in acetone at 22° C. Titration reflected a residual acidity of 0.1209 meq. acid/gram. The product exhibited shape memory behavior when exposed to a temperature of between 40° C. and 52° C. during the shape memory testing procedure described herein. The Young's modulus, E', was 107 MPa at 22° C. and 20.7 MPa at 37° C. When tested in accordance with the cytotoxicity testing described herein the product was nontoxic grade 0 to mammalian cells.

EXAMPLE 6

The procedures detailed in Example 4 and Example 5 were repeated with 27.4 grams of the intermediate prepared as described in Comparative Example 2 and 72.6 grams of the intermediate prepared and described in Comparative Example 3 as starting ingredients.

After cooling for one hour in the mold, the product was removed from the mold yielding a disk of nominally 2 mm thickness. It was optically clear. Within 24 hours at 22° C., the product was no longer optically clear. The product swelled in acetone at 22° C. Titration reflected a residual acidity of 0.1052 meq. acid/gram. The product exhibited shape memory behavior when exposed to a temperature of between 32° C. and 45° C. during the shape memory testing procedure described herein. The Young's modulus, E', was 7.2 MPa at 22° C. and 2.6 MPa at 37° C. When tested in accordance with the cytotoxicity testing described herein the product was nontoxic grade 0 to mammalian cells.

EXAMPLE 7

The following components were placed into a 250 ml glass beaker: 35.0 grams sebacic acid, 8.59 grams ethylene glycol, and 3.19 grams glycerol. The beaker and its contents were placed in a vacuum oven set at 130° C. A 100 mm diameter Petri dish that was treated with a Teflon™ mold release agent was also placed in the oven to preheat it. The initially heterogeneous solid-liquid mixture transformed to a low viscosity fluid over the course of two hours. After four hours, the fluid mixture was mixed with a magnetic stirrer for three minutes and then poured into the preheated Petri dish. The Petri dish and sample were placed in a vacuum oven set at 130° C. A vacuum was applied and polymerization continued for 4,320 minutes. Then the oven power was turned off and the oven and product allowed to cool while maintaining reduced pressure. When the product cooled to ambient temperature, the pressure was increased to atmospheric. The product was removed from the Petri dish to yield a disk of nominally 2 mm thickness.

Upon cooling to 21° C., the product was not optically clear. It was not soluble in acetone, but it swelled in acetone. Titration reflected a residual acidity of 1.450 meq. acid/gram. The product exhibited shape memory behavior when exposed to a temperature of between 51° C. and 55° C. during the shape memory testing procedure described herein.

EXAMPLE 8

The procedure detailed in Example 7 was repeated with the following starting ingredients: 35.0 grams sebacic acid, 8.06 grams ethylene glycol, and 3.98 grams glycerol.

Upon cooling to 21° C., the product was not optically clear. It was not soluble in acetone, but it swelled in acetone. Titration reflected a residual acidity of 0.7091 meq. acid/gram. The product exhibited shape memory behavior when exposed to a temperature of between 40° C. and 48° C. during the shape memory testing procedure described herein.

EXAMPLE 9

The procedure detailed in Example 7 was repeated with the following ingredients: 35.0 grams sebacic acid, 7.52 grams ethylene glycol, and 4.78 grams glycerol.

Upon cooling to 21° C., the product was not optically clear. It was not soluble in acetone, but it swelled in acetone. Titration reflected a residual acidity of 0.6899 meq. acid/gram. The product exhibited shape memory behavior when exposed to a temperature of between 35° C. and 41° C. during the shape memory testing procedure described herein.

EXAMPLE 10

The following components were placed into a 400 ml glass beaker: 50.0 grams sebacic acid, 10.74 grams ethylene glycol and 6.83 grams glycerol. The beaker was loosely covered with aluminum foil and its contents were placed in a vacuum oven set at 125° C. The initially heterogeneous solid-liquid mixture transformed to a low viscosity fluid over the course of two hours. The fluid mixture was mixed with a magnetic stirrer for two minutes and then returned to the vacuum oven at 125° C. A vacuum was applied, and polymerization continued for 1,000 minutes before the pressure was increased to atmospheric and the sample was mechanically stirred for two minutes. The vacuum of was reapplied for 50 minutes. The mixture then was transferred to two 125 mm preheated Teflon™ crystallizing dishes. One dish contained about 30 grams of sample, while the other contained about 23 grams. The samples were returned to the vacuum oven under reduced pressure and set at about 130° C. These conditions were maintained for 3,100 minutes. The oven power then was turned off and the oven and product cooled to 28° C. while maintaining reduced pressure. Pressure then was increased to atmospheric and the product removed from the oven and the crystallizing dishes to yield two disks of nominally 2 mm thickness.

Upon cooling to ambient temperature, the product was not optically clear. It was not soluble in acetone, but it swelled in acetone. Titration reflected a residual acidity of 0.7591 meq. acid/gram. The product exhibited shape memory behavior when exposed to a temperature of between 34° C. and 38° C. during the shape memory testing procedure described herein. When tested in accordance with the cytotoxicity testing described herein, the product was found to be cytotoxic to mammalian cells Grade=4.

EXAMPLE 11

A 125 mm diameter Teflon™ crystallizing dish was charged with 10.0 grams of the intermediate reaction product of Example 1. The dish containing the semicrystalline intermediate was placed in a vacuum oven at 130° C. After fifteen minutes, the liquid intermediate was distributed evenly over the dish surface by gently rocking the dish thereby causing the liquid intermediate to flow and cover the entire dish bottom surface. Nitrogen gas was charged to the oven at a relatively high rate while the temperature was maintained at 130° C. After polymerizing for 2,400 minutes under these conditions, the nitrogen gas flow was stopped and the pressure was reduced. After polymerizing for 1,440 minutes under these conditions, the pressure was increased to atmospheric and the dish containing the polymerized product was removed from the vacuum oven and placed on a lab benchtop at 22° C. to cool.

Upon cooling, the product was not optically clear. The product was not soluble in acetone, but it swelled in acetone. Titration reflected a residual acidity of 0.2170 meq. acid/gram. The final product exhibited shape memory behavior when exposed to a temperature of between 42° C. and 48° C. during the shape memory testing procedure described herein.

Shape memory behavior was also demonstrated in this product by "cold drawing" the sample at ambient temperature (about 21° C.). The product was found to yield when stretched in uniaxial tension or when deformed by bending. It yielded at a uniaxial tensile strain of about 0.10 when stretched at a rate of 25.4 mm/min. The sample was subjected to an elongation of 100% and retained its deformed shape and dimensions after the deforming force was removed. The cold drawn deformed product then was heated to 57° C. Within 30 seconds, the product's original undeformed shape and dimensions were recovered.

EXAMPLE 12

The procedure described in Example 1 was repeated with the following ingredients: 101.125 grams sebacic acid, 21.730 grams ethylene glycol and 13.81 grams glycerol.

At room temperature the reactants formed a heterogeneous mixture of solid and liquid phases. As temperature was increased to about 149° C., the mixture became a homogeneous liquid. Time and process parameters were recorded when all material was a single phase liquid. Byproduct water vapor evolving from the reactor was condensed and collected in a volumetric receiving tube graduated in 0.1 cc increments. In total, 15.9 cc of water was collected. The intermediate reaction product was 117 grams of white waxy material, corresponding to 96.9% of the theoretical yield. While cooling to ambient temperature, the product was not optically clear. Titration reflected a residual acidity of 0.522 meq. acid/gram. The intermediate reaction product was soluble in acetone at room temperature.

The second stage polymerization was performed by placing a charge of 19.4 grams of the intermediate reaction product prepared as described above, into 125 mm diameter Teflon™ crystallizing dish at 22° C. The Teflon™ mold containing the intermediate was placed in a vacuum oven with the temperature set at 120° C. The pressure was initially set at atmospheric pressure. The solid semicrystalline intermediate melted to form a clear viscous liquid within fifteen minutes. The liquid was distributed over the dish by rocking it. Pressure then was reduced. After 1,080 minutes, oven pressure was raised to atmospheric and a small sample (sample 1) was taken before the product was returned to the vacuum oven under reduced pressure and at 120° C. The sampling process was repeated at 1,440 minutes (sample 2), 2,460 minutes (sample 3) and 5,305 minutes (sample 4) total time. The residual acidity for each sample is reported in Table 1, below.

Upon cooling to 23° C., the samples were not optically clear. All were insoluble in acetone, but swelled in acetone. All four samples exhibited shape memory behavior. When tested in accordance with the cytotoxicity testing described herein, Sample 4 was found to be nontoxic, Grade=0 to mammalian cells.

TABLE 1

| Polymerization Time | | Residual Acidity (meq./gram) |
|---|---|---|
| Cumulative Time (min.) | Segment Time (min.) | |
| 1080 | 1080 | 0.2586 |
| 1440 | 360 | 0.2582 |
| 2460 | 1020 | 0.1157 |
| 5305 | 2845 | 0.0909 |

EXAMPLE 13

An intermediate reaction product was prepared according to the process described in Example 1, above. The reactants consisted of 101.125 grams sebacic acid, 21.730 grams ethylene glycol and 13.81 grams glycerol. Upon heating, the reactants formed a homogeneous liquid at 165° C. A total of 13.2 cc byproduct water was collected.

Upon cooling to ambient temperature, the intermediate reaction product became a white waxy material that was not optically clear. 120 grams of intermediate was recovered, which corresponds to 97.2% of the theoretical yield. The intermediate reaction product was soluble in acetone. Titration reflected a residual acidity of 1.518 meq. acid/gram.

A 125 mm Teflon™ crystallizing dish was charged with 35 grams of the intermediate reaction product at room temperature. The sample was placed in an oven at 120° C. under vacuum. The sample was polymerized for 13,968 minutes before cooling and raising pressure to ambient conditions of 22° C.

Upon cooling, the product was not optically clear. It was insoluble in acetone, but swelled in acetone. Titration reflected a residual acidity of 0.0280 meq. acid/gram. The product exhibited shape memory behavior when exposed to a temperature of 37° C. When tested in accordance with the cytotoxicity testing described herein, it was nontoxic, Grade=0 to mammalian cells.

EXAMPLE 14

A 125 mm Teflon™ crystallizing dish was charged with a 35 gram sample of the intermediate reaction product prepared according to the method of Example 13. Polymerization was conducted at a temperature of 120° C. and under a vacuum for 5,760 minutes. The sample was removed from the oven and cooled at ambient temperature to 22° C.

Upon cooling, the product was not optically clear. It was insoluble in acetone, but swelled in acetone. Titration reflected a residual acidity of 0.2294 meq. acid/gram. The product exhibited shape memory behavior when exposed to a temperature of 37° C. When tested in accordance with the cytotoxicity testing described herein, the product was nontoxic, Grade=0 to mammalian cells.

EXAMPLE 15

The final product of Example 12 (Sample 4) was sterilized by gamma radiation at a dose of 25 kGy. Titration reflected a residual acidity of 0.0960 meq. acid/gram. The product exhibited shape memory behavior after sterilization when exposed to a temperature of 37° C. When tested in accordance with the cytotoxicity testing described herein, the product was found to be nontoxic, Grade=0, to mammalian cells.

EXAMPLE 16

A semicrystalline intermediate reaction product having a residual acidity of 0.8690 meq. acid/gram was prepared according to the procedure described in Example 1.

A 125 mm diameter Teflon crystallizing dish was charged with 8.3 grams of this intermediate and placed in a vacuum oven at a temperature of 140° C. The vacuum oven pressure was equal to atmospheric pressure. The semicrystalline intermediate melted to a clear viscous liquid within five minutes and a vacuum applied. Polymerization continued under these conditions for 5,460 minutes. The pressure then was increased to atmospheric and the Teflon™ dish and its contents were removed from the vacuum oven and placed on a lab benchtop to cool at 22° C.

Upon cooling, the product was optically clear. The product was not soluble in acetone, but it swelled in acetone. Titration reflected a residual acidity of 0.0210 meq. acid/gram. The product did not exhibit shape memory behavior when subjected to the shape memory test procedure described herein.

EXAMPLE 17

25.0 grams sebacic acid (Aldrich, 99%), 1.918 grams ethylene glycol (Aldrich, 99.8% anhydrous) and 8.5367 grams glycerol (Aldrich, 99.5%+ spectrophotometric grade) were placed into a 250 ml glass beaker. The beaker and its contents were placed in a vacuum oven set at 120° C. A 100 mm diameter glass Petri dish was also placed in the vacuum oven to preheat it. The inner surfaces of the dish were treated with a Teflon™ mold release agent. The initially heterogeneous solid-liquid mixture transformed to a low viscosity fluid over the course of three hours. The fluid mixture was mixed with a magnetic stirrer for several minutes and then it was poured into the preheated Petri dish and placed back in the vacuum oven at 120° C. under reduced pressure. Polymerization was continued under these conditions for 4,080 minutes. The pressure then was increased to atmospheric and the oven and product cooled to 23° C.

Upon cooling to ambient temperature, the product was optically clear. The product was not soluble in acetone, but it swelled in acetone. Titration reflected a residual acidity of 0.2064 meq. acid/gram. The product did not exhibit shape memory behavior when subjected to the shape memory test procedure described herein.

EXAMPLE 18

Additional samples of the crosslinked polymer compositions were prepared using alternative diols. The following monomer components were placed into a 0.5 liter glass reactor: 101.25 grams sebacic acid (Aldrich, 99%), 28.54 grams 1,3-propanediol (Aldrich, 99.6%+ anhydrous), and 11.51 grams glycerol (Aldrich, 99.5%+ spectrophotometric grade). The reactor was equipped with agitation, heating, vapor condensing, liquid volume measuring, temperature regulating, temperature measuring and nitrogen gas purging capabilities. The procedure described in Example 1 was followed.

Initially, the reactants formed a heterogeneous solid/liquid mixture at room temperature. As temperature was increased, the reactants became a homogeneous liquid mixture at about 117° C. Time and process parameters were recorded when all material in the reactor formed a single phase liquid. Water vapor was condensed and collected in a volumetric receiving tube graduated in 0.1 cc increments. In total, 14.0 cc of water was collected.

Upon cooling to ambient temperature, the intermediate reaction product was not optically clear. 123.3 grams of a white waxy intermediate reaction product, corresponding to a 96.9% yield, was recovered in the first stage of polymerization. The intermediate reaction product was soluble in acetone. Titration reflected a residual acidity of 1.0528 meq. acid/gram.

In the second polymerization stage, a charge of 20.0 grams of the intermediate reaction product was placed into a 125 mm diameter Teflon™ crystallizing dish at 22° C. This was placed in a vacuum oven with the temperature set at 120° C. and pressure equal to atmospheric pressure. The solid semicrystalline intermediate melted to a clear viscous liquid within five minutes before pressure was reduced. Polymerization continued for 6,060 minutes under these conditions, before the temperature was decreased to 22° C.

After increasing the pressure to atmospheric, the product was removed from the Teflon™ mold yielding a disk of 125 mm diameter of nominally 2 mm thickness. Upon cooling, the product was not optically clear. The product was not soluble in acetone, but it swelled in acetone. Titration reflected a residual acidity of 0.174 meq. acid/gram. The product exhibited shape memory behavior when exposed to a temperature of between 42° C. and 47° C. during the shape memory testing procedure described herein.

EXAMPLE 19

The following monomer components were placed into a 0.5 liter glass reactor: 101.25 grams sebacic acid (Aldrich, 99%), 33.75 grams 1,4-butanediol (Aldrich, Reagent Plus>99%) and 11.51 grams glycerol (Aldrich, 99.5%+ spectrophotometric grade). The reactor was equipped with agitation, heating, vapor condensing, liquid volume measuring, temperature regulating, temperature measuring and nitrogen gas purging capabilities. The procedure described in Example 1 was followed.

Initially, the reactants formed a heterogeneous solid/liquid mixture at room temperature. As temperature was increased, the reactants became a homogeneous liquid mixture at about 118° C. Time and process parameters were recorded when all material in the reactor formed a single phase liquid. The water vapor was condensed and collected in a volumetric receiving tube graduated in 0.1 cc increments. In total, 13.5 cc of water was collected.

Upon cooling to ambient temperature, the intermediate reaction product was not optically clear. 130.5 grams of a white waxy intermediate reaction product was collected, corresponding to a 98.1% yield. The intermediate reaction product was soluble in acetone. Titration reflected a residual acidity of 1.1276 meq. acid/gram.

In the second stage, a charge of 29.3 grams of the intermediate reaction product was placed into a 125 mm diameter Teflon™ crystallizing dish at 22° C. This was placed in a vacuum oven with the temperature set at 120° C. and a vacuum was applied. The solid semicrystalline intermediate melted to a clear viscous liquid within four hours. Polymerization continued for 5,760 minutes under these conditions, before the temperature was decreased to 22° C.

Upon cooling, the product was not optically clear. After increasing the pressure to atmospheric, the product was removed from the Teflon™ mold yielding a disk of 125 mm diameter of nominally 2 mm thickness. The product was not soluble in acetone, but it swelled in acetone. Titration reflected a residual acidity of 0.2344 meq. acid/gram. The product exhibited shape memory behavior when exposed to a temperature of between 49° C. and 51° C. during the shape memory testing procedure described herein.

EXAMPLE 20

26.0 grams sebacic acid (Aldrich, 99%), 5.59 grams ethylene glycol (Aldrich, 99.8% anhydrous)and 3.55 grams glycerol (Aldrich, 99.5%+ spectrophotometric grade) were combined in a 250 ml glass beaker. The beaker was loosely covered with aluminum foil and placed in a vacuum oven set at 127° C. The heterogeneous reaction mixture transformed to a homogeneous liquid after 165 minutes. After an additional 240 minutes, 22.7 grams of the liquid reactive mixture was transferred from the 250 ml glass beaker into a 1,000 ml glass beaker that was preheated and treated with Teflon™ mold release agent. Sodium chloride (NaCl) crystals (187.5 grams) were poured onto the liquid phase, thereby creating a salt bed through which the low viscosity liquid phase percolated. The solids volume fraction of the sodium chloride phase was about 0.85. Pressure was reduced and temperature was increased to 127° C. The polymerization continued under these conditions for 5,305 minutes. Then the oven power was turned off and the material cooled to 22° C. under vacuum.

The sodium chloride was extracted from the intermediate reaction product by rinsing with reverse osmosis water (conductivity<5 microsiemens/cm) until the water washings had a conductivity less than 400 microsiemens/cm. The porous reaction product was now compliant when probed with a finger. The cellular void space of the porous reaction product was filled with water.

The water-wet intermediate reaction product was placed in a vacuum oven at 22° C. and pressure was decreased with a vacuum pump to dry it to a constant weight. After drying in this manner, 19.7 grams of the dried product was collected, which corresponds to an approximately 100% yield after accounting for byproduct water from the polymerization operation. The porous reaction product was disk shaped and approximately 16 mm thick.

Figure 19:
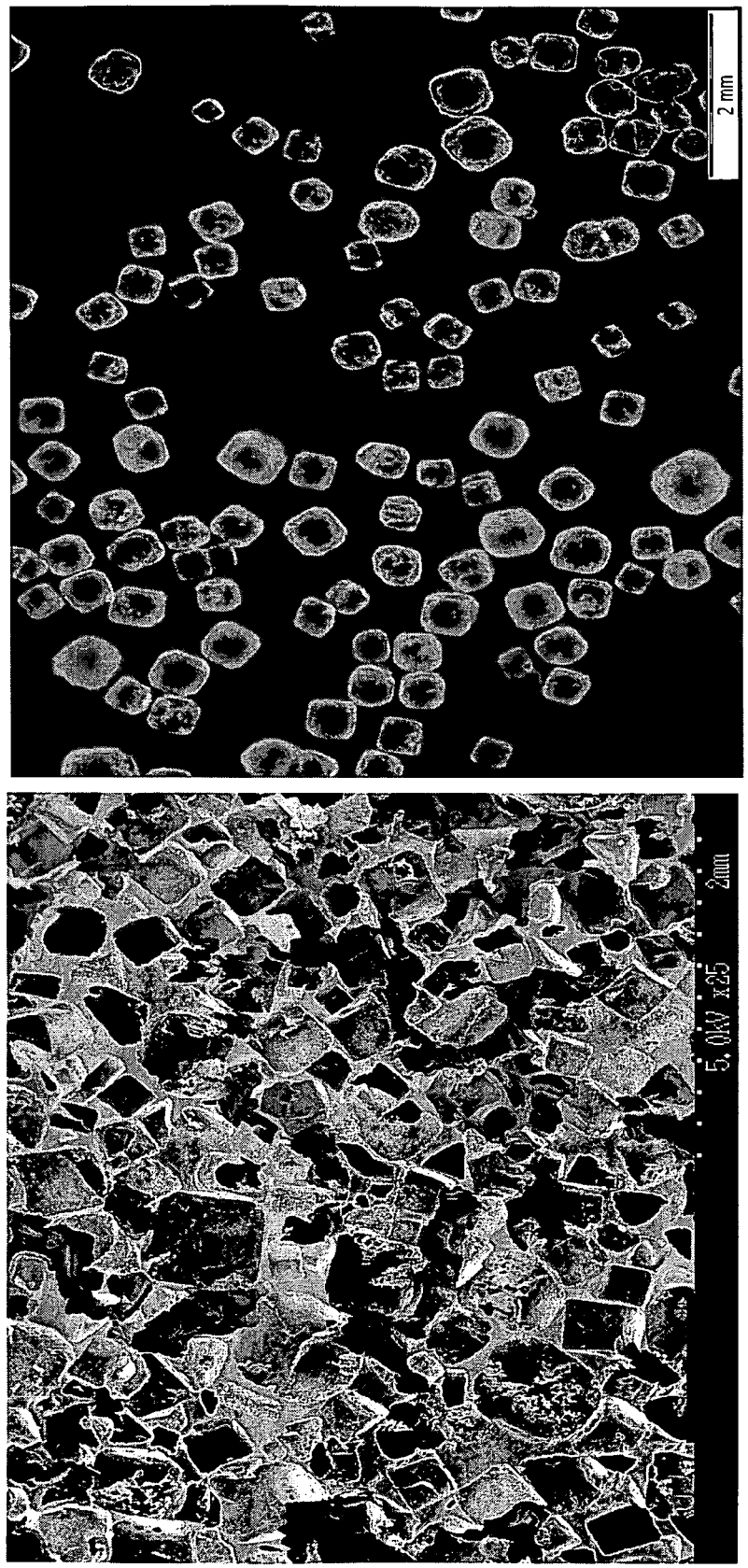
FIG. 19 is a scanning electron microscope view of an exemplary porous composition of Example 20.

The final foam product has a density equal to 0.17±0.02 g/cc, indicating that the product was about 85% by volume void space. It was examined with a scanning electron microscope (SEM) and the cellular geometry resembled the sodium chloride crystal shapes and dimensions as shown in FIG. 19. Differential scanning calorimetry (DSC) showed that the foam product had a glass transition temperature, $T_g$, of about −35° C., was semicrystalline at 22° C., and was totally amorphous at temperatures above 36° C. The foam product was not soluble in acetone, but it swelled in acetone. Titration with potassium hydroxide indicated residual acidity of 1.0280 meq. acid/gram. The foam product exhibited shape memory behavior in a 37° C. water bath.

EXAMPLE 21

101.125 grams sebacic acid (Aldrich, 99%), 21.730 grams ethylene glycol (Aldrich, 99.8% anhydrous) and 13.81 grams glycerol (Aldrich, 99.5%+ spectrophotometric grade) were polymerized according to the procedures described in first polymerization stage of Example 1 to form an intermediate reaction product. The intermediate reaction product had a residual acidity of 0.522 meq. acid/gram.

20.0 grams of the intermediate reaction product was combined with 40.0 grams of acetone in a four ounce glass jar at 23° C. The mixture then was stirred with a magnetic stirrer and a clear homogeneous low viscosity intermediate-acetone solution formed within one hour.

185.0 grams of sodium chloride (NaCl) crystals was poured into a 125 mm diameter Teflon™ crystallizing dish and distributed to create a uniformly thick salt bed through which a low viscosity liquid phase could percolate. The Teflon™ crystallizing dish and salt bed were placed in a 120° C. vacuum oven and pressure was decreased to dry the salt bed for two hours. The salt bed was removed from the vacuum oven and placed in a 45° C. forced air oven for an additional two hours of drying.

The intermediate-acetone solution was poured onto the salt bed. The intermediate-acetone solution percolated through the salt bed. A total of 57.1 grams of the 33.33% by weight intermediate solution was transferred and its volume occupied the salt bed void space and an excess volume layer sat above the salt bed. The acetone was evaporated at 45° C. The intermediate-imbibed salt bed was transferred from the 45° C. forced air oven to a 120° C. vacuum oven and pressure was reduced. These polymerization conditions were maintained for 1,500 minutes before the crosslinked polymer imbibed salt bed sample was removed from the vacuum oven and placed in a refrigerator at 0° C. After one hour, the sample was removed from the refrigerator and placed on a lab benchtop at 23° C. The sample was removed from the Teflon™ crystallizing dish, and was found to be stiff to the touch.

The sodium chloride was extracted from the intermediate composite by washing with reverse osmosis water (conductivity<5 microsiemens/cm) at 21° C. until the water washings also had a conductivity less than 5 microsiemens/cm. With the salt removed, the sample was compliant when probed.

The water-wet porous intermediate reaction product was dried overnight, then vacuum dried at 37° C. for four hours, and then polymerized in a vacuum oven at 120° C. and pressure reduced. Polymerization continued under these conditions for an additional 7 days. The foam product was removed from the oven and placed on a lab benchtop at 22° C. to cool. The dry foam final product was a 10 mm thick disk weighing 17.5 grams.

The cooled foam had a density equal to 0.15±0.02 g/cc, indicating that the product had about 85% by volume void space. The foam product was not soluble in acetone, but it swelled in acetone. Titration reflected a residual acidity of 0.1000 meq. acid/gram.

When tested in accordance with the cytotoxicity testing described herein, the foam product was found to be nontoxic, grade=0 to mammalian cells. The foam product exhibited shape memory behavior. A right circular cylinder of the foam was deformed by biaxial compression at 45° C. and subsequently cooled to 22° C. The foam maintained this deformed shape for 21 hours then, when subsequently heated to 45° C., the foam exhibited shape memory behavior.

EXAMPLE 22

A further example of the foam compositions was prepared according to the procedure similar to that described in Example 21. The monomer components were 202.25 grams of sebacic acid (Aldrich, 99%), 43.46 grams ethylene glycol (Aldrich, 99.8% anhydrous) and 26.26 grams glycerol (Aldrich, 99.5%+ spectrophotometric grade). The intermediate reaction product had a residual acidity of 0.5547 meq. acid/gram.

20 grams of the intermediate reaction product was combined with 70 grams of acetone, and the resulting intermediate/acetone solution (75.8 grams) was poured onto a salt bed comprising 138 grams of salt having a particle size of less than 70 mesh and a bulk density of 0.945 g/cc. The acetone was evaporated at 45° C. for 24 hours.

The intermediate-imbibed salt bed was further polymerized at 137° C. and under vacuum for 2,880 minutes. The sodium chloride was extracted by rinsing with reverse osmosis water as in the previous examples.

The resulting foam had a density of 0.24 g/cc, indicating that it was comprised of about 75% void space. The product was not soluble in acetone, but swelled in acetone. Titration reflected residual acidity of 0.2005 meq. acid/gram.

The foam also was examined by DSC and was totally amorphous at temperatures equal or above 38° C. The crosslinked foam exhibited shape memory behavior.

EXAMPLE 23

A further example of the foam compositions was prepared according to the procedure described in Example 21. The intermediate reaction product had a residual acidity of 0.6712 meq. acid/gram. The intermediate reaction product was combined with acetone and the resulting intermediate/acetone solution was poured onto a salt bed (Aldrich, A.C.S. reagent grade>99.0%). The procedures for acetone evaporation, polymerization, salt extraction, water evaporation and further polymerization described in Example 21 were followed to produce 19 grams of crosslinked polyesterfoam of density equal to 0.16 g/cc. The crosslinked foam exhibited shape memory behavior at 37° C.

EXAMPLE 24

20.3 grams of the intermediate of Example 16 was combined with 40.0 grams of acetone in a four ounce glass jar at 21° C. A magnetic stir bar was added to the mixture; the jar was capped and stirred with a magnetic stirrer until a clear homogeneous low viscosity solution formed (within about one hour). The intermediate-acetone solution was placed in a 45° C. forced air oven.

185.0 grams of sodium chloride (NaCl) crystals was poured into a 125 mm diameter Teflon™ crystallizing dish and distributed to create a uniformly thick salt bed through which a low viscosity liquid phase could percolate. The Teflon™ crystallizing dish and salt bed were placed in a 40° C. vacuum oven and pressure decreased to dry the salt bed for about 3 hours.

The salt bed was removed from the vacuum oven, after increasing the pressure to atmospheric, and 58.0 grams of the intermediate-acetone solution was poured onto the salt bed. The intermediate-acetone solution percolated through the salt bed and occupied the salt bed void space and an excess volume layer sat above the salt bed.

The crystallizing dish and its contents were placed in a 45° C. forced air oven for 20 hours. Then, the intermediate-imbibed salt bed was transferred to a 40° C. vacuum oven and a vacuum applied. These conditions were maintained for 3 hours. Then the temperature was increased to 130° C. over the course of about 2 hours, and polymerization continued under these conditions for an additional 5,520 minutes.

After increasing pressure to atmospheric pressure, the Teflon™ crystallizing dish and polymer imbibed-salt bed removed from the vacuum oven and cooled to 0° C. After 1 hour, the Teflon™ crystallizing dish and polymer imbibed salt bed was warmed to 22° C. Thereafter, the polymer imbibed salt bed was removed from the Teflon™ crystallizing dish.

Next, the sodium chloride was extracted from the intermediate composite by washing with reverse osmosis water (conductivity<5 microsiemens/cm) at 22° C. until the water washings had a conductivity less than 30 microsiemens/cm. With the salt removed, the sample was compliant when probed.

The water-wet intermediate product was air dried over 2 days, then vacuum dried for 19 hours at 37° C. Then, the pressure was increased to atmospheric and the foam product was removed from the oven and cooled to 22° C.

The dry foam product was recovered in the shape of a disk having a thickness of nominally 10 mm. The foam had a density of 0.14 g/cc, indicating that the product was comprised of about 85% by volume void space.

The foam product exhibited a crystalline melting point ($T_m$) in the range 2° C.<$T_m$<9° C. The foam product was not soluble in acetone, but it swelled in acetone. The residual acidity was found to be 0.2377 meq/gram. The foam product did not exhibit shape memory behavior.

EXAMPLE 25

An aqueous dye solution was prepared by combining 1.60 grams Indigo Carmine crystals and 100 ml of reverse osmosis water at 22° C. The resultant dye solution was transferred to a four ounce glass jar. Several right circular cylinders of the dried foam product of Example 23 having a diameter of about 5 mm were transferred to the dye solution. In like manner, several right circular cylinders of the dried foam product of Example 22 having a diameter of about 4 mm were transferred to the dye solution. These foam objects were alternately compressed and decompressed several times to imbibe the foam with the dye solution. The jar containing the solution and solution imbibed foam objects was capped and placed in an oven at 50° C. for one hour. Then the jar and its contents were removed from the oven and placed in a lab hood at 22° C. to cool. After an additional two hours, the solution-imbibed foam objects were removed from the solution and placed on aluminum weighting dishes and then transferred to a 50° C. vacuum oven under reduced pressure to dry for 16 hours. Then pressure was increased to atmospheric and the dried foam objects transferred to a lab hood at 22° C. to cool. After cooling, all foam objects were a deep blue color.

Several 4 mm diameter cylindrical samples of the porous polymer, some containing Indigo Carmine dye and some undyed were evaluated. The samples were placed between two aluminum plates with their long axis parallel to the plates. The top plate was weighted down by a large brass block. This metal and porous polymer assembly were placed into a 60° C. temperature chamber for 30 minutes. The temperature of the chamber was reduced to 0° C. and remained an additional 30 minutes. The temperature was increased to 25° C., and the metal and porous polymer assembly was removed. The porous polymer samples were extracted from between the aluminum plates and were now compressed to a metastable state of approximately 1 mm in thickness.

The dyed, and non-dyed, compressed metastable porous samples were irradiated with the frequency doubled Nd:YAG laser source. The blue dye has a broad absorption band centered at approximately 600 nm. The wavelength of light emitted from a frequency doubled Nd:YAG source is 532 nm. Measurements were previously made of the blue-dyed foam's UV-VIS spectrum in a reflection mode and the spectrum indicated that the blue-dyed foam was strongly absorptive at 532 nm.

Each sample was placed into the beam path of the laser for 30 seconds. Three samples of blue-dyed foam were irradiated by the laser in this manner. In each instance the blue-dyed foam demonstrated uniform shape and dimensional recovery in response to the laser stimulus.

Samples of non-dyed foam were, in like manner, irradiated for 60 seconds as a control experiment. The undyed foam did not demonstrate a dimensional shape recovery. As a further control experiment, one sample of dyed and compressed porous polymer was placed onto a hot plate to determine if shape recovery would occur. This sample of foam expanded to a cylinder with a diameter of approximately 4 mm demonstrating substantial recovery.

EXAMPLE 26

136.98 grams sebacic acid (Aldrich, 99%), 34.62 grams ethylene glycol (Aldrich, 99.8% anhydrous) and 22.02 grams glycerol (Aldrich, 99.5%+ spectrophotometric grade) were combined in a glass reactor. The reactor was equipped with agitation, heating, vapor condensing, liquid volume measuring, temperature regulating, temperature measuring and nitrogen gas purging capabilities.

Initially, the reactants formed a heterogeneous solid/liquid mixture at room temperature. As temperature was increased, the reactants became a homogeneous liquid mixture at about 127° C. Time and process parameters were recorded once all material in the reactor formed a single phase liquid. Byproduct water vapor was condensed and collected in a volumetric receiving tube graduated in 0.1 cc increments; 21.9 cc total water was collected. Upon cooling to ambient temperature, the intermediate product formed was not optically clear. The intermediate reaction product was soluble in acetone. Titration reflected a residual acidity of 0.4305 meq. acid/gram.

Three foam compositions then were prepared from this uncrosslinked intermediate reaction product. The uncrosslinked intermediate was melted and charged to three 50 ml plastic beakers. To each beaker was added a quantity of 4,4'-methylenebis(phenyl isocyanate), (MDI) (Huntsman, FW=250.26 grams/mole, MP=37° C., RUBINATE® 44) that had been heated to 50° C., such that the weight fraction of MDI in the first beaker was 0.15, the weight fraction of the second was 0.25 and the third was 0.35. Each then was mixed for 30 seconds with a centrifugal mixing apparatus (Thinky AR250) and then placed in a 120° C. oven for 40 minutes. The mixtures reacted and gas was generated in-situ, resulting in the creation of three foam compositions.

Upon cooling to room temperature, it was apparent that all three foams were stable. The foam volume increased as the weight fraction of MDI in the composition increased.

The foam sample corresponding to a MDI weight fraction equal to 0.15 was examined to probe its physical, mechanical and shape memory properties. The sample was insoluble in acetone. The foam was of the open cell kind. The foam density at 22° C. was about 0.35 grams/cc suggesting that it comprised about 65% by volume air or void space.

The sample was heated from 20° C. at a rate of 2° C./min. It exhibited two endothermic transitions ($T_1$ and $T_2$) over the temperature range 30° C.<$T_1$<42° C. and 50° C.<$T_2$<65° C. The Young's modulus, E', was 7 MPa at 25° C. and 0.35 MPa at about 57° C. The foam sample demonstrated shape memory behavior at 85° C.

EXAMPLE 27

Another foam example was created from the intermediate reaction product of 101.13 grams sebacic acid (Aldrich, 99%), 21.73 grams ethylene glycol (Aldrich, 99.8% anhydrous) and 13.81 grams glycerol (Aldrich, 99.5%+ spectrophotometric grade). During the first stage polymerization, 15.0 cc water was collected. Upon cooling to ambient temperature, the product was not optically clear. It was soluble in acetone. Titration reflected a residual acidity of 0.6712 meq. acid/gram.

Three foam compositions then were prepared from the uncrosslinked intermediate reaction product. Following the procedures described in Example 26, heated MDI (Huntsman, FW=250.26 grams/mole, MP=37° C., RUBINATE® 44) was added to the molten intermediate reaction product such that the weight fraction of MDI in each of three beakers corresponded to 0.15 in the first beaker, 0.25 in the second, and 0.35 in the third. These combinations then were mixed with a centrifugal mixing apparatus (Thinky AR250) for 30 seconds and then placed in a 120° C. oven for 40 minutes. During this time, the mixtures reacted and gas was generated in-situ, resulting in the creation of three foam compositions.

Upon cooling to room temperature, all three of the foams were stable. The foam volume increased as the weight fraction of MDI in the composition increased.

EXAMPLE 28

Another foam example was created from the intermediate reaction product of 202.25 grams sebacic acid (Aldrich, 99%), 36.93 grams ethylene glycol (Aldrich, 99.8% anhydrous) and 23.48 grams glycerol (Aldrich, 99.5%+ spectrophotometric grade). During the first stage polymerization, 27.4 cc water was collected. Upon cooling to ambient temperature the product was optically not clear. The intermediate was soluble in acetone.

Three foam compositions then were prepared from the uncrosslinked intermediate reaction product. Following the procedures described in Example 26, heated MDI (Huntsman, FW=250.26 grams/mole, MP=37° C., RUBINATE® 44) was added to molten intermediate reaction product such that the weight fraction of MDI in each of beaker corresponded to 0.15, 0.25 or 0.35. These combinations then were mixed with a centrifugal mixing apparatus (Thinky AR250) for 30 seconds and then placed in a 120° C. oven for 40 minutes. During this time, the mixtures reacted and gas was generated in-situ resulting in the creation of three foam compositions.

Upon cooling to room temperature, all three of the foams were stable. The foam volume increased as the weight fraction of MDI in the composition increased.

EXAMPLE 29

The uncrosslinked intermediate reaction product of Example 21 was added to a glass vessel containing acetone such that the intermediate reaction product concentration was six percent by weight. The mixture then was heated to 45° C. and stirred. Within four hours, a homogeneous solution was obtained. The solution was removed from the heat source and cooled to room temperature.

An ePTFE nonwoven web was imbibed with the solution to form a composite prepreg. The ePTFE nonwoven was made in accordance with the teachings of Bacino, U.S. Pat. No. 5,476,589. A wire wound rod coating process was used to imbibe the ePTFE. The intermediate polymer solution was fed directly onto the unsupported ePTFE nonwoven web and was metered with a #29 wire wound coating rod. The line speed was 3 m/min. and the wrap angle was approximately 145 degrees on the coating rod. As the solution was being applied, an ACCUPLY backing material (obtained from Accurate Plastics, Yonkers, N.Y.) was applied to the ePTFE web such that the polymer solution coated side was oriented towards the backing material. After imbibing the ePTFE with the polymer intermediate solution, the acetone was evaporated in a convection oven.

Using the same process settings, the opposite side of the ePTFE nonwoven web was coated with polymer intermediate solution. In this second coating step, a #8 wire wound rod was used to coat the exposed ePTFE. After coating, the acetone was evaporated in a convection oven.

A multi-layer composite structure was fabricated by wrapping the composite prepreg tape onto a stainless steel mandrel. The mandrel cross-section was essentially square; it had four flat sides measuring 30 mm by 60 mm. The intermediate corners were each rounded to a 5 mm arc. A fluorinated ethylene propylene (FEP) release film was first applied to the mandrel to prevent the prepreg composite tape from bonding to the mandrel. The prepreg composite tape was applied to the mandrel while the mandrel rotated at a speed of 10 rpm. The process continued for 8 minutes to create a multilayer composite structure consisting of eighty layers of the prepreg composite tape.

The mandrel and composite assembly then was placed in a vacuum oven at 135° C. and vacuum applied. The imbibed polymer intermediate was further polymerized for 5,040 minutes under these conditions before the temperature was reduced to approximately 22° C. and the pressure was increased to atmospheric pressure. The imbibed polymerized intermediate was crosslinked and semicrystalline at room temperature. The resulting 80 layer composite structure was divided into four sections by cutting the composite with a razor blade at the corners of the mandrel. The sections were removed from the mandrel and FEP release layer, yielding four flat multilayer composite sheets 60 mm long, 30 mm wide, and about 0.3 mm thick. The composite sheets had a density of about 1.1 g/cc.

The multilayer composite structure exhibited shape memory behavior when exposed to a temperature between about 40° C. and about 55° C. during the shape memory testing procedure (non-porous) described herein.

EXAMPLE 30

A thermally activated release mechanism was constructed from a composite consisting of an ePTFE and the crosslinked polyester composition described herein. The mechanism could be provided, for example, at the distal end of a catheter to either release or capture objects within a body.

The composite prepreg tape of Example 29 was cut with a $CO_2$ laser into 0.254 mm wide strips. The 0.254 mm prepreg strips were wrapped circumferentially around a conical mandrel that had been fashioned by chamfering the end of a brass rod. The prepreg tape wrapped mandrel was placed in a vacuum oven at 120° C. for 24 hours under reduced pressure. Upon cooling to room temperature, the imbibed polymerized intermediate of the composite object was not optically clear. As discussed above in connection with Example 21, the imbibed polymerized intermediate was crosslinked.

The composite was removed from the mandrel, but remained in a conical shape in the absence of external forces or support from the mandrel. A 0.127 mm diameter nitinol wire was inserted into the center of the composite cone parallel to its longitudinal axis. The wire and composite assembly was placed into a 60° C. water bath for several minutes, and the composite assembly was radially compressed against the wire. While compressed, the composite assembly and wire were placed into a 0° C. temperature chamber for several minutes. The sample then was removed from the 0° C. temperature chamber, and the compressive forces relieved. The composite kept its compressed shape (i.e., a cylinder with the nitinol wire running through its long axis).

The ends of the nitinol wire were connected to a DC power supply which was set to output 9 volts. The output was activated, resistive losses in the wire resulted in a temperature increase in the nitinol. This increase in temperature caused the composite to assume a larger diameter permitting release of the nitinol wire. The shape memory composite was substantially restored to its original conical structure.

EXAMPLE 31

Another composite embodiment exhibiting shape memory properties was constructed by combining poly(glycolide-co-trimethylenecarbonate) (PGA/TMC) nonwoven material with the crosslinked polyester composition. The PGA/TMC nonwoven web used to make the composite prepreg was made in accordance with the teachings of Hayes in U.S. Pat. Nos. 6,165,217 and 6,309,423.

About 4 grams of the uncrosslinked semicrystalline intermediate of Example 21 was sectioned into small granules with a razor blade. A polyethylene release film was taped flat to a 152.4 mm×508 mm thin stainless steel sheet. A 101.6 mm×101.6 mm drawdown bar with a 0.2 mm gap was placed on the polyethylene sheet, and the entire assembly was placed in an oven at 130° C. for about ten minutes. The assembly was removed from the oven and the uncrosslinked semicrystalline intermediate granules were placed in front of the drawdown bar. A heat gun was gently waved over the uncrosslinked semicrystalline granules until they became a molten mass. The drawdown bar then was pulled slowly along the surface of the release liner to create a uniform molten thin film of the amorphous uncrosslinked intermediate. The PGA/TMC nonwoven web was placed onto the amorphous molten intermediate film. The viscous intermediate wet and imbibed the PGA/TMC nonwoven web resulting in a prepreg sheet of about 0.203 mm thickness.

After cooling to room temperature, a razor blade was used to cut 8 rectangular prepreg strips from the prepreg sheet. Each sheet had dimensions of 80 mm length×12.7 mm width. These prepreg strips then were assembled into two multilayer stacks of four layers per stack. The stacks were placed on a 203.2 mm×203.2 mm glass plate; the plate having been covered with 0.076 mm thick PTFE film. Another PTFE film and glass plate were placed on top of the stacks. A 678 gram stainless steel weight was placed on top of the stack to compress the strips together.

The entire assembly was placed in a vacuum oven at 145° C., and the pressure was reduced. These conditions were maintained for 2.5 hours before the pressure was increased to atmospheric and the temperature reduced. The stainless steel weight was removed and pressure decreased. These conditions were maintained for an additional 18.5 hours. Then pressure was again increased to atmospheric and the top glass plate and PTFE film removed. Pressure again was decreased with a vacuum pump. These polymerization conditions maintained for an additional 1,440 minutes. The temperature was decreased to room temperature and pressure was increased to atmospheric. In this way, two rectangular shaped flat composite structures having dimensions of 80 mm length×12.7 mm width×0.64 mm thickness were fabricated from the prepreg sheet described above. The composite's density at room temperature was about 1.2 g/cc.

The multilayer composite structure exhibited shape memory behavior when exposed to a temperature between about 39° C. and about 46° C. during the shape memory testing procedure (non-porous) described herein.

EXAMPLE 32

The following components were placed into a first 250 ml glass beaker: 35.0 grams sebacic acid, 8.59 grams ethylene glycol, and 3.19 grams glycerol (first sample). Into a second 250 ml glass beaker were placed 35.0 grams sebacic acid, 7.52 grams ethylene glycol, and 4.78 grams glycerol (second sample). The beakers and their contents were placed in a vacuum oven set at 120° C. Two 100 mm diameter Petri dishes were treated with a Teflon™ mold release agent and placed in the oven to preheat.

The initially heterogeneous solid-liquid mixture transformed to a low viscosity fluid over the course of an hour. After about 1 hour, approximately 22.7 grams of each of the fluid mixtures was poured into separate preheated Petri dishes. Each Petri dish and sample was placed in a vacuum oven set at 130° C. A vacuum was applied and polymerization continued for about 4,320 minutes.

Then the oven power was turned off and the oven and product cooled while maintaining reduced pressure. Pressure then was increased to atmospheric and the product cooled to ambient temperature. The samples were removed from the Petri dishes to yield two disks. Titration reflected residual acidities of 1.450 meq. acid/gram and 0.6899 meq. acid/gram, respectively for sample 1 and sample 2.

A piece of sample 1 was cut into a rectangular strip 2.0 mm wide and 30.0 mm long and 1.5 mm thick. Two similarly sized pieces of sample 2 also were obtained. A composite was fashioned by placing the two sample 2 strips on top of the sample 1 strip and compressing in thickness using a heated Carver press (Carver, Inc., Wabash, Ind.) at 130° C., under significant compressive force for one hour. The compressed composite was cooled to room temperature then removed from the press. The composite had a nominal thickness of approximately 3 to 4 mm.

The composite was placed into a curved beam shape by placing the sample and a tube in an oven at 60° C. At this temperature, the now-amorphous composite was fashioned to the curvature of the tube and held in place with tape. The composite then was placed into a freezer to cool the material to a temperature of 0° C.

Figure 20:
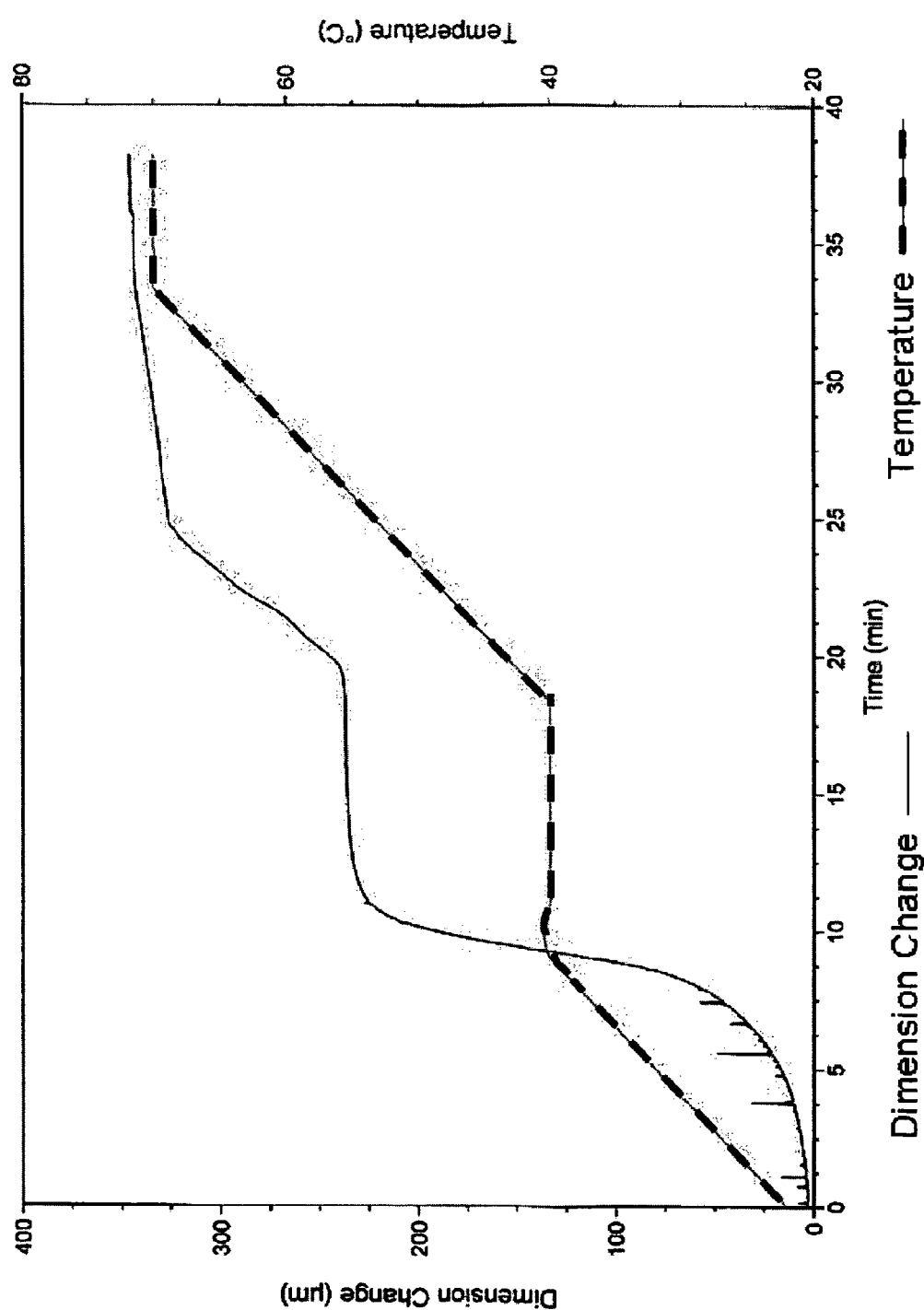
FIG. 20 is a graph of dimension change and temperature for the exemplary composite of Example 24.

From the cooled, curved sample, a 13.97 mm long sample was cut. This sample was subjected to a stepped thermal program, which raised the temperature at 5° C./min from room temperature to 40° C., held this temperature for 10 minutes, and then raised the temperature to 70° C., again at 5° C./min. The dimension change is shown in FIG. 20.

EXAMPLE 33

The porous reaction product of Example 23 was first compressed and set into a metastable state. A 6.45 cm² piece of semicrystalline foam of nominally 10 mm thickness was placed into a 60° C. water bath for several minutes. The now amorphous foam was removed from the water bath and immediately placed between two aluminum plates which were spaced apart by two 2.54 mm thick aluminum spacers. A clamp was used to hold the plates together. The assembly was allowed to set overnight at room temperature. The now semicrystalline metastable foam was removed from between the plates and placed under vacuum for five minutes to remove residual water.

The compressed metastable foam then was cut via a $CO_2$ laser into 3.05 mm diameter cylinders. The heat generated by the laser caused the temperature of the foam to rise which resulted in shape recovery of the material. A 0.127 mm diameter nitinol wire was pushed through the center of the recovered now amorphous foam cylinder parallel to its long axis.

The wire and foam were placed into a 60° C. water bath for 5 minutes. Co-radial compression (with the cylinder and the wire) was applied to the foam. The foam was placed into a 0° C. temperature chamber for 10 minutes while compression was maintained. The now semicrystalline metastable foam was compressed tightly around the nitinol wire.

The wire-metastable foam assembly was inserted into the in-vitro aneurysm model and fed into the simulated aneurysm. The simulated aneurysm was a bubble of approximately 6.35 mm diameter formed in a clear plastic tube, of approximately 70 mm in length with an inner diameter of approximately 3.05 mm wall. The wire then was connected to a DC power supply which was set to 9 volts. The output voltage was applied, which caused resistive heating of the nitinol wire. The heat generated resulted in shape recovery of the foam composition, which in turn filled the simulated aneurysm/bubble. The wire then was withdrawn.

EXAMPLE 34

A vascular closure device model was constructed in the following manner: A 101.6 mm×101.6 mm piece of nominally 7.62 mm thick foam of Example 22 was compressed in thickness using a heated Carver press (Carver, Inc., Wabash, Ind.) at 65° C., under one ton clamping force for about 3 hours. The compressed foam was cooled to room temperature then removed from the press. Once removed, the foam had a nominal thickness of approximately 1.143 mm. The compressed foam then was cooled below room temperature with compressed air. The foam then was die cut to form a compressed plug using a 2.388 mm inner diameter hypodermic tube (available from Small Parts, Miami Lakes, Fla.) that was taper ground to form sharp leading edge. The compressed plug was removed from the end of the hypodermic cutting tube and again cooled below room temperature.

An intraluminal delivery device for the closure device included an expanding braided shaft having a central lumen. An actuating wire was disposed within the lumen. The actuating wire was attached to the braided shaft at the distal end. The braided shaft is substantially covered by a polymeric material which prevented radial expansion, elongation or shortening of the braid. Near the distal end a section of the braided shaft was not covered and unrestrained. This uncovered portion separated the polymeric cover into a distal portion and a proximal portion. An overtube covered the proximal portion of the polymeric cover. When the overtube and proximal end of the device was held and the actuating wire was pulled proximally, the distal end of the device moved proximally and the braided shaft expanded within the unrestrained portion to form a disk like projection extending perpendicularly to the axis of the delivery device. The compressed plug was threaded over the proximal polymeric cover and pushed distally by the over tube. The actuating wire then was pushed distally to retract the braid.

A simulated vascular system to be repaired was constructed of a silicone tube, which simulated an artery. The tube was placed in an outer tube filled with gelatin to simulate the surrounding tissue. An introducer was inserted into the silicone tube. Insertion of the introducer created the simulated wound to be closed.

The vascular closure device was delivered to the repair site via the introducer. The braid was positioned beyond the injury site before the braid was expanded. The closure device was pushed distally against the expanded braid using the overtube. With the closure device locked in position between the overtube and the braid, the assembly was withdrawn until the braid contacted the inner wall of the simulated artery. Warm saline was provided via the introducer to activate the shape memory property of the closure device. The introducer then was withdrawn. The unrestricted closure device then expanded to provide a patch at the simulated injury site. The polymer foam was disposed between the outer wall of the simulated artery and the simulated surrounding tissue. After placing the device, the braid was retracted by pushing the actuating wire distally. After retraction, the entire delivery device was withdrawn. The closure device was held in place by the over tube, which was ultimately removed.

EXAMPLE 35

A 175 mm×8 mm ID, 24 end braid of 0.127 mm nitinol wire (Medical Murray, North Barrington, Ill.) was placed on an 8 mm OD SS tube (McMaster Carr, New Brunswick, N.J.). A 100 mm width section of composite prepreg of Example 29 was continuously wrapped in the machine direction around the nitinol braid and tube 6 to 8 full revolutions. This construct then was heated to 160° C. under vacuum for 10 hours and then cooled with liquid $CO_2$. When the temperature of the resulting assembly reached room temperature, the mandrel was removed.

The assembly then was heated in an oven at 50° C. for 10 minutes. Upon removal from the oven, the assembly was immediately pulled in axial tension by grabbing the two opposing ends of the nitinol braid and stretching, thereby reducing the diameter, and increasing the length of the composite-nitinol braid. Then, the assembly was cooled using liquid $CO_2$. Cooling fixed the braid and composite in an elongated metastable state. The assembly retained the metastable state at room temperature. Upon heating the assembly to 45° C., the assembly shortened in length and expanded in diameter, thereby substantially recovering its original dimensions. This assembly operated in this manner multiple times.

EXAMPLE 36

The hemostatic properties of the foam were demonstrated in a porcine liver laceration model. Several foams were selected for testing. The materials differed in pore size and handling properties which are detailed in Table 2, below. The samples used were in the form of cylinders approximately 15 mm in diameter and between 6 mm and 10 mm in length. Cotton gauze was used as a comparison.

TABLE 2

| Material | Pore Size | State at 22° C. | Shape Stored In Sample | Hemostasis |
|---|---|---|---|---|
| Cotton Gauze | N/A | N/A | N/A | − |
| Example 20 | Large | Semicrystalline | No | + |
| Example 21 | Large | Semicrystalline | No | +/− |
| Example 22 | Small | Semicrystalline | No | +/+ |
| Example 23 | Large | Semicrystalline | Yes | ++ |
| Example 24 | Large | Amorphous | No | +/− |

− no hemostasis within 5 minutes with compression;
+/− hemostasis within 3 minutes with compression;
+ homeostasis within 1 minute with compression;
++ hemostasis within 5 seconds with no compression One untreated Yucatan swine with normal average clotting time was used in the study. A midline incision was used to expose the liver. A 13 mm diameter trephine was used to core holes approximately 1 cm deep in the liver. The wounds bled profusely for 5 seconds after which the sample materials were inserted into the wound. No external pressure was applied initially. The time to cessation of bleeding through the wound was measured. After five minutes, the material was removed from the wound, placed in 10% neutral buffered formalin, and processed for histological analysis.

All foam materials were easy to handle and apply to the wound, and all filled with blood and produced hemostasis within 3 minutes. The foam of Example 22, which had small pores, and the foam of Example 23 (which had stored shape) produced hemostasis within 5 seconds after application to the wound without applying compression to the wound. The foam of Example 20 produced hemostasis within one minute after applying compression. Slow bleeding was observed surrounding Examples 21 and 24 after one minute of compression, but hemostasis was complete after two minutes without further compression.

Histologic evaluation of the retrieved samples was conducted. The interstices of Example 22 foam were filled with fewer erythrocytes and a greater proportion of proteinaceous fluid then the other examples. In those specimens the microstructure contained pools of essentially intact blood. There was also no evidence of frank toxicity.

Test Methods

Shape Memory:

The shape memory behavior of porous products may be probed as follows: right circular cylinders are extracted from the dried foam product at 22° C. using a cork borer having an internal diameter of 15.4 mm. The initial or default state length and diameter dimensions of each cylinder are measured to the nearest 0.01 mm and respectively designated, $L_0$ and $D_0$. The initial or default state cylinder volume, $V_0$, is calculated as follows:

$$V_o = \frac{1}{4}\pi D_o^2 L_o.$$

Next, a metastable state is created by deforming the right circular cylinder in uniaxial compression while the polymer foam is in its amorphous state to a linear compressive strain, $\epsilon$, in the range $0.3 \leq \epsilon \leq 0.5$. After deformation, the temperature is decreased to 0° C., while holding constant the compressive strain. The temperature and compressive strain are maintained for 25 hours to 40 hours before increasing temperature to 22° C. After about one hour, the external compressive force is decreased to zero. The deformed or metastable state dimensions of the cylinder are measured to the nearest 0.01 mm and respectively designated $L_d$ and $D_d$. The metastable state volume, $V_d$, of each cylinder may be calculated and designated as follows:

$$V_d = \frac{1}{4}\pi D_d^2 L_d.$$

The metastable state linear compressive strain, $\epsilon_{L,d}$, and volumetric compressive strain, $\epsilon_{V,d}$, may be calculated as follows:

$$\varepsilon_{L,d} = \frac{(L_d\ L_o)}{L_o}$$

$$\varepsilon_{V,d} = \frac{(V_d\ V_o)}{V_o}$$

To determine if the samples are dimensionally stable, the metastable state cylinders are stored at 22° C. in the absence of an external force field for eight days.

To determine if the metastable state foam cylinders substantially recover their original or default state dimensions via a thermal stimulus, each is placed in a warm aqueous solution at a temperature of 30° C. to 100° C. The metastable state foam cylinders then are placed into the solution for one hour. After one hour, the dimensions of the cylinders are measured to the nearest 0.01 mm and respectively designated, $L_r$ and $D_r$. The volume of the shape recovered foam cylinders may be calculated as follows:

$$V_r = \frac{1}{4}\pi D_r^2 L_r$$

The measurements are made while the foam is water saturated. Next, the saturated foam cylinders are dried in a vacuum oven at 30° C. to 100° C. to constant weight. The linear dimensions and volume of the shape recovered foam cylinders are compared to that of the original or default state cylinders. Shape memory behavior is demonstrated if the sample recovers at least 50% of its original dimension.

The shape memory behavior of non-porous products may be evaluated in a three step shape recovery experiment. First, a right rectangular prism of the sample is deformed by bending the sample around a brass pipe at a temperature at which the sample is in an amorphous state. Second, the sample is cooled to room temperature, and the deforming force is removed to determine if the bent shape is maintained. Third, the sample is heated to determine if it tends to revert to its shape before deformation. The procedure is described in more detail below.

At 22° C., strips of adhesive tape (150 mm×20 mm) are placed with the adhesive side up on a flat benchtop. A right rectangular prism (35 mm×5 mm×2 mm) of the sample to be tested is placed onto the tape such that it has a long axis oriented parallel to the long axis of the tape and about 50 mm of tape projected from one end of the sample. The sample is secured to the tape.

One end of the exposed tape is attached to a brass thin walled pipe having an outer diameter of 20.7 mm so that the long axis of the prism and tape is orthogonal to the pipe axis. The pipe and sample or samples to be tested are placed in an oven at 90° C. for 30 minutes prior to deforming them. Each sample then is deformed by wrapping the tape around the pipe and securing the free end of the tape to the pipe. The entire assembly is cooled at 22° C.

The deforming force is removed by removing the tape from the sample and pipe assembly. Samples that do not maintain their shape (i.e., do not maintain a metastable state) are determined not to have shape memory. Samples that do maintain their deformed shape (i.e., do maintain a metastable state) may be further evaluated to determine the stability of the deformed shape. Such samples are stored in deformed or metastable state.

The samples then are tested to determine if the original state would be substantially recovered upon applying an activating stimulus. Approximately 10 mm long samples of the deformed prisms are cut from the sample. These 10 mm long samples are placed across quartz knife edges spaced 5 mm apart. The samples are heated from 20° C. at 1° C./min. Samples that substantially recover their original state at a temperature of less than about 100° C. are considered to have shape memory properties. Samples substantially recovering their original state between about 30° C. and 60° C. were considered to have particular applicability in human medical applications.

Modulus

Elastic moduli, such as Young's modulus, can be measured with a dynamic mechanical analyzer. (DMA) at strains of less than 1% as a function of temperature. The temperature ramp rate is 1° C./min. The frequency is 1 Hz.

Cytotoxicity Testing:

Minimum Essential Media (MEM) may be used to evaluate the presence of cytotoxic extractables and their effect on living mammalian cells. A polymer sample is extracted with the extraction media at 37° C.±1° C. for 24 to 30 hours. L929 mouse fibroblast cells are exposed to the test extract at 37° C. for 72 hours. After staining, cells are examined with the aid of a light microscope. A visual assessment of the biological response considers the state of health of a monolayer of the cells. Cytotoxicity is scored on a scale of 0 (negative response) to 4 (more than 75% of cells morphologically changed). Results of 2 to 4 are cytotoxic.

Polymer samples are not rinsed prior to extraction. Samples are extracted using 1 gram of sample to 5 ml MEM with 5% newborn calf serum, 292 mg/l L-glutamine in distilled deionized water, 1.2 g/l sodium bicarbonate, 3.6 g/l HEPES and 100 µg/ml gentamycin.

Natural rubber latex is used as a positive control and it is extracted in the same manner as the test samples. A negative control or blank extraction is also included.

Sufficient quantity of L929 mouse fibroblast cells are grown in wells for 24 to 96 hours. Cells are trypsinized and cell suspensions are prepared. Each cell suspension is diluted with MEM Growth Media to a concentration of $1\text{-}3\times10^5$ cells/ml. The diluted cell suspension is gently mixed and used to seed 35 mm test wells. The cells are incubated at 37° C.±1° C. in an atmosphere of 5%±1% $CO_2$ and a relative humidity of greater than about 90%. Incubation continues until a confluent monolayer forms (≧80% confluent).

The MEM Growth Media is aspirated from the cells in the test wells and is replaced with the same volume of test sample extract. Test wells then are incubated under the conditions specified above for an additional 72±3 hours. After incubation, sufficient dilute neutral red in sterile phosphate buffered saline is added to the cells in each well to yield a final dye concentration of about 50 µg/ml. These preparations are then returned to the incubator under the specified conditions for 1-2 hours. After this final incubation, wells are stained red. Viable cells are stained red. However, nonviable cells are not stained, rather these cells remain clear. Cells are examined by optical microscopy at a magnification of 100× to 400×, and cytotoxicity is rated on a scale of 0 to 4 using the following cytotoxicity scoring table. All positive controls are toxic at a titer of about 1.4 to about 1.64 dilution. All negative controls have a score of zero.

Cytotoxicity Scoring Table

| Score | Microscopic Observations Following Addition Of Neutral Red And Incubation As Outlined Above |
|---|---|
| 0 | Negative response, cell morphology and density are like negative controls. |
| 1 | Similar to control but ≦25% of cells are granular, swollen or crenated. |
| 2 | >25% of cells are granular, swollen or crenated, and/or 25-49% are dead, lysed or sloughed. |
| 3 | 50% to 74% of the cells are dead, lysed or sloughed cells. |
| 4 | 75% to 100% of the cells are dead, lysed or sloughed cells. |

Scores of 0 or 1 are considered nontoxic. Scores of 2 to 4 are considered toxic.

While particular embodiments of the present invention(s) have been illustrated and described herein, the present invention(s) should not be limited to such illustrations and descriptions. It should be apparent that changes and modifications may be incorporated and embodied as part of the present invention(s) within the scope of the following claims.

The inventions claimed are:

1. A crosslinked polycondensation product of:
   a. polyol comprising saturated aliphatic triol, and saturated aliphatic diol, in which the moles of saturated aliphatic triol divided by the total moles of polyol is in the range of about 0.2 to about 0.8, and
   b. at least one saturated linear aliphatic diacid or derivative thereof, in which the total moles of polyol divided by the moles of diacid is in the range of about 0.9 to about 1.2.

2. The crosslinked polycondensation product of claim 1, in which said polyol comprises glycerol and ethylene glycol.

3. The crosslinked polycondensation product of claim 1, in which said at least one saturated linear aliphatic diacid comprises sebacic acid.

4. The crosslinked polycondensation product of claim 1, in which said diacid or derivative thereof comprises at least one diester of a saturated linear aliphatic diacid in which the total moles of polyol divided by the moles of diester of saturated linear aliphatic diacid is in the range of about 0.9 to about 1.2.

5. The crosslinked polycondensation product of claim 1, in which said diacid or derivative thereof comprises at least one diacyl halide of a saturated linear alphatic diacid in which the total moles of polyol divided by the moles of diacyl halide of saturated linear aliphatic diacid is in the range of about 0.9 to about 1.2.

6. The crosslinked polycondensation product of claim 1 comprising randomly linked moieties.

7. The crosslinked polycondensation product of claim 6, in which the moles of saturated aliphatic triol divided by the total moles of polyol is in the range of about 0.20 to about 0.65.

8. The crosslinked polycondensation product of claim 1 comprising block or multi-block linked moieties.

9. A crosslinked polycondensation product of:
   polyol comprising glycerol and ethylene glycol, in which the moles of glycerol divided by the total moles of polyol is in the range of about 0.2 to about 0.8, and
   sebacic acid, in which the total moles of polyol divided by the moles of sebacic acid is in the range of about 0.9 to about 1.2.

10. A crosslinked polycondensation product of:
    polyol comprising glycerol and 1,3 propanediol, in which the moles of glycerol divided by the total moles of polyol is in the range of about 0.2 to about 0.8, and
    sebacic acid, in which the total moles of polyol divided by the moles of sebacic acid is in the range of about 0.9 to about 1.2.

11. A crosslinked polycondensation product of:
    polyol comprising glycerol and 1,4 butanediol, in which the moles of glycerol divided by the total moles of polyol is in the range of about 0.2 to about 0.8, and
    sebacic acid, in which the total moles of polyol divided by the moles of sebacic acid is in the range of about 0.9 to about 1.2.

12. The crosslinked polycondensation product as in one of claims 1-11 having a residual acidity range of less than about 1.0 milliequivalents of acid per gram of product.

13. The crosslinked polycondensation product as in one of claims 1-11 that is non-cytotoxic.

14. The crosslinked polycondensation product as in one of claims 1-11 that exhibits shape memory behavior.

15. A porous polymer comprising the crosslinked polycondensation product of claims 1-11.

16. A polymer composition having a backbone consisting essentially of linked ester units, A, B, and C, wherein said linked ester units are of the formulae:

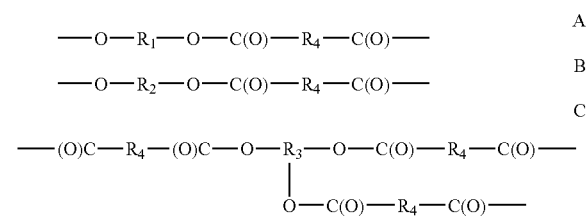

where $R_1$ has the formula:

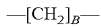

where $R_2$ has the formula:

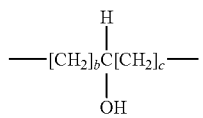

$R_3$ has the formula:

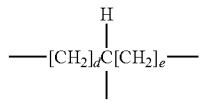

$R_4$ has the formula:

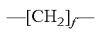

where a and f are, independently integers between 2 and 35, and b, c, d and e are, independently, integers between 1 and 35, and wherein β and φ are given by the formulae:

$$\beta = \frac{[\text{moles } R_1 + \text{moles } R_2 + \text{moles } R_3]}{[\text{moles } R_4]}$$

$$\varphi = \frac{[\text{moles } R_2 + \text{moles } R_3]}{[\text{moles } R_1 + \text{moles } R_2 + \text{moles } R_3]}.$$

and satisfy the following expressions:

$$0.9 \leq \beta \leq 1.2,$$

$$0.20 \leq \varphi \leq 0.80.$$

17. The polymer composition of claim 16, in which the moieties are randomly linked, and wherein φ is in the range of 0.20 to 0.65.

18. The polymer composition of claim 17, in which φ is in the range of 0.20 to 0.50.

19. The polymer composition of claim 16, in which the moieties are block or multi-block linked moieties.

20. The polymer composition of claim 19, which is at least partially phase separated.

21. The polymer composition of claim 19, in which the following expression is satisfied:

$$0.50 \leq \phi \leq 0.80.$$

22. The polymer composition of claim 16, in which the $R_1$ moiety comprises about 4 to about 30 mol % of the polymer composition.

23. The polymer composition of claim 16, in which the $R_2$ moiety and the $R_3$ moiety comprise about 4 to about 30 mol % of the polymer composition.

24. The polymer composition of claim 16, in which the $R_4$ moiety comprises about 20 to about 30 mol % of the polymer composition.

25. The polymer composition of claim 16, in which the ester linkages comprise about 35 to about 55 mol % of the polymer composition.

26. The polymer composition of claim 16, in which the polymer composition is crosslinked.

27. The polymer composition of claim 16 having less than 1.0 milliequivalents of a residual acid per gram of the polymer composition.

28. The polymer composition of claim 16 that is non-cytotoxic.

29. The polymer composition of claim 16 that exhibits shape memory behavior.

30. The polymer composition of claim 16, which exhibits crystallization upon cooling at a rate of 2° C./min. from a temperature of about 100° C. to a temperature of about 20° C.

31. The polymer composition of claim 16, having at least a semicrystalline structure at temperatures between 20° C. and 25° C., and having an amorphous structure at temperatures between about 30° C. and about 100° C.

32. The polymer composition of claim 16, in which $R_1$ has at most 10 carbon atoms, $R_2$ has at most 4 carbon atoms, $R_3$ has at most 4 carbon atoms and $R_4$ has at most 10 carbon atoms.

33. The polymer composition of claim 16, in which $R_1$ comprises 2 carbon atoms.

34. The polymer composition of claim 16, in which $R_1$ comprises 3 carbon atoms.

35. The polymer composition of claim 16, in which $R_1$ comprises 4 carbon atoms.

36. The polymer composition of claim 16, in which $R_2$ comprises 3 carbon atoms.

37. The polymer composition of claim 16, in which $R_3$ comprises 3 carbon atoms.

38. The polymer composition of claim 16, in which $R_4$ comprises 8 carbon atoms.

39. The polymer composition of claim 16, further comprising urethane and urea linkages which comprise about 15 mole % or less of the polymer composition, and in which non-polymeric void spaces are defined within the polymer composition.

40. The polymer composition of claim 39, in which the urethane linkages consist essentially of:

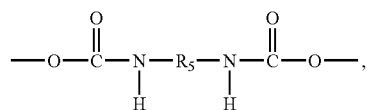

in which the urea linkages consist essentially of:

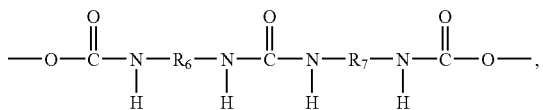

where $R_5$, $R_6$, and $R_7$, are each independently a divalent aromatic or aliphatic moiety.

* * * * *